United States Patent
Mui et al.

(10) Patent No.: US 12,016,963 B2
(45) Date of Patent: *Jun. 25, 2024

(54) FRESHENING COMPOSITIONS WITH ALKOXYLATED PHENOLS

(71) Applicant: The Procter & Gamble Company, Cincinnati, OH (US)

(72) Inventors: Michael David O'Young Mui, Mason, OH (US); Kevin Lee Kott, Cincinnati, OH (US); Jennifer Lea Rinker, Hamilton, OH (US); Bonny Kay Lui, Cincinnati, OH (US); Gregory Scot Miracle, Liberty Township, OH (US); Karunakaran Narasimhan, Mason, OH (US); George Kavin Morgan, III, Hamilton, OH (US); David Wesley Brogden, Cincinnati, OH (US); Jennifer Beth Allison, Cincinnati, OH (US); Andrea C. Keenan, Pottstown, PA (US); Daniel S. Miller, Phoenixville, PA (US); Theodore Tysak, Ambler, PA (US); Raymond Schill, Maple Glen, PA (US)

(73) Assignee: The Procter & Gamble Company, Cincinnati, OH (US)

( * ) Notice: Subject to any disclaimer, the term of this patent is extended or adjusted under 35 U.S.C. 154(b) by 72 days.

This patent is subject to a terminal disclaimer.

(21) Appl. No.: 16/864,175

(22) Filed: May 1, 2020

(65) Prior Publication Data
US 2020/0353113 A1  Nov. 12, 2020

Related U.S. Application Data

(60) Provisional application No. 62/845,894, filed on May 10, 2019.

(51) Int. Cl.
*A61L 9/14* (2006.01)
*A61L 2/22* (2006.01)
*A61L 9/01* (2006.01)

(52) U.S. Cl.
CPC .................... *A61L 2/22* (2013.01); *A61L 9/01* (2013.01); *A61L 9/14* (2013.01); *A61L 2202/26* (2013.01)

(58) Field of Classification Search
CPC ..... A61L 2/22; A61L 9/01; A61L 9/14; A61L 2202/26; A61L 2209/132; A61K 8/39; A61K 8/86; A61Q 13/00; D06M 13/005
See application file for complete search history.

(56) References Cited

U.S. PATENT DOCUMENTS

| | | | |
|---|---|---|---|
| 4,261,922 A | 4/1981 | Kem | |
| 5,500,154 A | 3/1996 | Bacon et al. | |
| 7,179,775 B2 | 2/2007 | Foster | |
| 7,550,416 B2 | 6/2009 | Woo | |
| 9,119,973 B2 | 9/2015 | Warr et al. | |
| 9,260,817 B2 | 2/2016 | Williams | |
| 9,499,770 B2 | 11/2016 | Morgan, III et al. | |
| 9,511,165 B2 | 12/2016 | Vlad | |
| 9,676,545 B2 | 6/2017 | Sunder et al. | |
| 2005/0124512 A1 | 6/2005 | Woo | |
| 2015/0217015 A1 | 8/2015 | Williams | |
| 2015/0252302 A1 | 9/2015 | Rieth et al. | |
| 2016/0067661 A1 | 3/2016 | Ahrens | |
| 2016/0096192 A1 | 4/2016 | Bush | |
| 2016/0333291 A1 | 11/2016 | Aida et al. | |
| 2016/0340607 A1 | 11/2016 | Amorelli et al. | |
| 2017/0137745 A1 | 5/2017 | Tang | |
| 2017/0247110 A1 | 8/2017 | Chappell | |
| 2017/0274110 A1 | 9/2017 | Nwachukwu | |
| 2018/0155658 A1 | 6/2018 | Lant et al. | |
| 2019/0093046 A1 | 3/2019 | Turner et al. | |
| 2019/0093047 A1 | 3/2019 | Yoshida | |

(Continued)

FOREIGN PATENT DOCUMENTS

| | | |
|---|---|---|
| EP | 2708593 A1 | 3/2014 |
| JP | S5770197 A | 4/1982 |
| JP | H10245782 A | 9/1998 |

(Continued)

OTHER PUBLICATIONS

Dow produces a wide range of glycol ether products consisting of P-Series glycol ethers and acetates (from propylene oxide) and E-Series glycol ethers and cetates (from ethylene oxide).2Pages.
"Dow Oxygenated Solvents", Product Overview and Selection Guide, 2018, 8 pages.
DOWANOL™ EPh Glycol Ether, Form No. 110-00591-0308, Mar. 2008, 2 pages.
All Office Actions; U.S. Appl. No. 16/864176.
U.S. Appl. No. 16/864,176, filed May 1, 2020, Miracle, et al.
Search Report; Serial No. PCT/US2020/070034; 12 Pages; dated Aug. 7, 2020.
Search Report; Serial No. PCT/US2020/070035; 12 Pages; dated Aug. 7, 2020.

*Primary Examiner* — Jessica Worsham
(74) *Attorney, Agent, or Firm* — Carolyn S. Powell; Abbey Alicia Lopez; George Henry Leal

(57) ABSTRACT

Freshening composition having at least 85% by weight of the freshening composition of water; at least 0.0015% of by weight of the freshening composition of alkoxylated phenol; and a perfume having at least 60% by weight of the perfume, Perfume Raw Materials having ClogP greater than 1.0. The alkoxylated phenol is according to Formula (I):

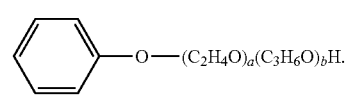

(I)

wherein a is a value selected from 3 to 15; b is a value selected from 0 to 12;
wherein the value of a+b, the degree of alkoxylation is from 3 to 15.

17 Claims, No Drawings

(56) References Cited

U.S. PATENT DOCUMENTS

2019/0194579 A1 6/2019 Miracle
2020/0353114 A1 11/2020 Miracle

FOREIGN PATENT DOCUMENTS

| JP | 2006328551 A | * | 12/2006 |
| WO | 2014043075 A1 | | 3/2014 |
| WO | 2018013450 A1 | | 1/2018 |

* cited by examiner

FRESHENING COMPOSITIONS WITH ALKOXYLATED PHENOLS

FIELD OF THE INVENTION

The present invention relates to freshening compositions having alkoxylated phenols and perfume raw materials (PRMs) in an aqueous carrier for providing freshness benefits.

BACKGROUND OF THE INVENTION

Freshening products for freshening fabrics or the air or reducing/eliminating malodors on fabrics and/or in the air are currently available. These products typically contain a freshening composition that includes perfume raw materials (PRMs), solvents, surfactants, and high levels of water. Having a wide variety of scent choices in freshening products enables consumers to find one that they like.

However, because of the hydrophobic nature of PRMs, surfactants and/or solvents are used to solubilize and emulsify the PRMs, especially given formulations with high levels of water. However, solvents and relatively high levels of surfactants, although help to emulsify particularly hydrophobic PRMs, may pose at least one of several challenges.

For example, although surfactants are used, the levels are to be minimized otherwise the surfactants may cause fabrics or surfaces to turn yellow or brown under natural light and/or make fabric or surfaces susceptible to soiling and/or change the consumer perception of how the fabric or surface feels. Solvent selection and levels are to be considered as they have limited ability to solubilize a wide range of PRMs, have environmental considerations, and may negatively impact scent. Additionally, many solvents used are high Volatile Organic Compounds (VOC). VOC materials pose challenges for negatively impacting scent as well as concerns around flashpoint regulations. Given these challenges, formulators typically have solvent and surfactant limitations, which in turn minimizes the use of relatively more hydrophobic PRMs. This reduces the breadth of available PRMs and thus scent experiences to users. These challenges are exacerbated when formulations contain especially high levels of water and/or high levels of relatively hydrophobic PRMs.

Therefore, there is a need for improved freshening compositions that provide a wide variety of scent experiences enabled by more hydrophobic PRMs while minimizing levels of surfactants.

SUMMARY OF THE INVENTION

The present invention relates to a freshening composition comprising:
a) at least 85% by weight of the freshening composition of water;
b) at least 0.0015% of by weight of the freshening composition of alkoxylated phenol; and
c) a perfume, wherein the perfume comprises at least 60% by weight of the Perfume Raw Materials having ClogP greater than 1;
d) wherein the alkoxylated phenol is according to Formula (I):

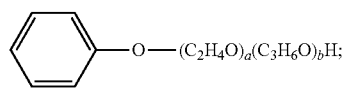

wherein a is a value selected from 3 to 15; b is a value selected from 0 to 12;
wherein the value of a+b, the degree of alkoxylation is from 3 to 15.

DETAILED DESCRIPTION

Perfume raw materials (PRMs) are typically formulated with water to make sprayable freshening compositions including but not limited to air freshening compositions, fabric freshening compositions or air and fabric freshening compositions. However, because of the hydrophobic nature of PRMs, solvents and/or surfactants are used to solubilize and emulsify the PRMs in compositions with high water content. Solvents suitable for solubilizing PRMs typically include alcohols, polyols and mixtures thereof.

The present invention is based on the surprising discovery that the freshening composition of the present invention comprising high levels of water, perfume and relatively low levels of alkoxylated phenol can improve solubility of a perfume having PRMs having a ClogP greater than 1.0 in water content thereby providing phase stable sprayable freshening compositions.

Having the combination of PRMs and alkoxylated phenol enables a phase stable sprayable freshening composition and a wider range of PRMs may be formulated. The alkoxylated phenol may be an ethoxylated phenol, a propoxylated phenol or combinations thereof. Experimental results using ethoxylated phenol as an example of alkoxylated phenol demonstrating the technical effect are described hereinbelow.

In the following description, the composition described is a fabric freshening composition. However, it is contemplated that the composition may be configured for use in a variety of applications to provide freshness on inanimate surfaces or in the air.

Prior to describing the present invention in detail, the following terms are defined for clarity. Terms not defined should be given their ordinary meaning as understood by a skilled person in the relevant art.

The term "freshening composition" as used herein refers to compositions for providing freshness on surfaces including inanimate surfaces or in the air.

The term "inanimate surface" as used herein refers to surfaces including but not limited to fabrics, carpets, household surfaces such as countertops, floors, garbage cans, ceilings, walls, carpet padding, air filters, and the like.

The term "Perfume Raw Materials" as used herein refer to perfume materials ("PRMs" or, singularly, "PRM").

The term "ClogP" as used herein refers to a calculated logP ("ClogP") value of a PRM. An octanol/water partition coefficient of a PRM is the ratio between its equilibrium concentrations in octanol and in water. The partition coefficients of the PRM used in a freshening composition may more conveniently be given in the form of its logarithm to the base 10, LogP. The ClogP is determined by a model that computes the octanol-water partition coefficient (logP or logKow) for general organic molecules based directly on molecular structure. LogP is a measure of the distribution of a solute between two immiscible liquid phases, octanol and water, and is generally used as a relative measure of the hydrophobicity of a solute. One way of computing LogP of a PRM is using the ACD/Labs LogP software module from Advanced Chemistry Development, Inc. Details of the calculation of logP can be found on the ACD/Labs website (https://www.acdlabs.com/products/percepta/predictors/logp/). LogP values of PRMs calculating using the ACD/

Labs LogP software module and the LogP values of PRMs are used in the selection of PRMs which are useful in the present invention as described hereafter in the Examples. However, it will be appreciated that another suitable way of measuring LogP is using the "ClogP" program from BioByte Corp (e.g., ClogP Version 4.0 and Manual 1999). CLOG P USER GUIDE, Version 4.0, BioByte Corp (1999) (http://www.bio-byte.com/bb/prod/clogp40.html). A further suitable way of measuring LogP is using CLOGP program from Daylight Chemical Information Systems, Inc. of Alison Viejo, Calif. The CLOGP Reference manual, Daylight Version 4.9, Release Date Feb. 1, 2008.

The term "sulfur-containing pro-perfume" as used herein refers to a type of pro-perfume compound that contains sulfur. The term "pro-perfume" as used herein refers to compounds resulting from the reaction of PRMs with other chemicals, which have a covalent bond between one or more PRMs and these chemicals. The PRM is converted into a new material called a pro-perfume compound, which then may release the original PRM (i.e. pre-converted) upon exposure to a trigger such as water or light or atmospheric oxygen. Suitable pro-perfume compounds and methods of making the same can be found in U.S. Pat. Nos. 7,018,978; 6,861,402; 6,544,945; 6, 093,691; 6,165,953; and 6,096,918.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

I. Freshening Composition

A freshening composition according to the present invention comprises water in a level of at least 85% by weight of the composition, alkyoxylated phenol in a level of at least 0.0015% by weight of the composition, and a perfume wherein the perfume comprises at least 60% by weight of perfume, of PRMs having a ClogP greater than 1. A technical effect of providing the alkoxylated phenol is that the perfume with at least 60% of PRMs have a ClogP greater than 1.0 may be formulated with high levels of water (at least 85%) to provide a freshening composition. The freshening composition is sprayable and the perfume remains solubilized to provide a phase-stable freshening composition that provides a consistent delivery of scent freshness in each spray. Without wishing to be bound by theory, use of alkoxylated phenols relative to use of traditional solvents such as ethanol to solubilize perfumes in freshening compositions is alkoxylated phenols have the combination of a phenol functional group and an ether functional group in the same molecule which provides unique solvency characteristics with both polar and non-polar properties. This surfactant-like structure gives alkoxylated phenols the ability to couple unlike liquid phases of ingredients used for freshening compositions (e.g. water and perfume as described hereinafter) and be miscible in a broad range of hydrophilic and hydrophobic solvents. It will be appreciated by a person skilled in the art that amounts of the alkoxylated phenols and the PRMs, and water may be configured to meet performance requirements as defined under Test Methods including Test Method for Measurement of Turbidity described hereinafter. In particular, it will be appreciated that the freshening composition may be configured with PRMs having ClogP greater than 1 at a low enough level with at least 0.0015% of alkoxylated phenol to meet the above performance requirements.

Components of a freshening composition of the present invention are described in the following paragraphs.

A. Water

A freshening composition of the present invention may comprise at least 85%, by weight of the composition of water. The water may be in an amount from 85% to 99.5%, from 90% to 99.5%, from 95% to 99.5%, 95%, or different combinations of the upper and lower percentages described above or combinations of any integer in the ranges listed above, by weight of the composition. The water may be distilled, deionized or tap water. Having high levels of water enable a sprayable freshening composition while minimizing any visible residues and/or stains on fabric articles.

B. Alkoxylated Phenol

The freshening composition has an alkoxylated phenol in a level of at least 0.0015% by weight of the composition. Alkoxylation is a chemical reaction that involves the addition of an epoxide which is an alkoxylating agent to another compound. Epoxides may be lower molecular weight epoxides (oxiranes) such as ethylene oxide, propylene oxide and butylene oxide. These epoxides are capable of reacting with a hydroxyl group generally under base catalysis, causing a ring opening and the addition of an oxyalkylene group. The resulting compound contains a hydroxyl group, so a varied number of moles of oxide can be added. Alkoxylation of a phenol-containing compound relates to the reaction of mixtures of an epoxide with the phenol containing compound which produces hydroxy alkyl phenyl ether compounds (also known as alkoxylated phenols). A phenol-containing compound has the following structure and the molecular formulae is $C_6H_5OH$.

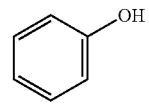

The alkoxylated phenol may comprise a structure according to Formula (I):

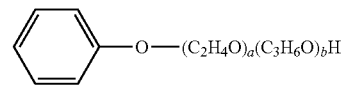

(I)

wherein a is a value selected from 3 to 15; b is a value selected from 0 to 12;

wherein the value of a+b, degree of alkoxylation is from 3 to 15.

Each of the a units of $(C_2H_4O)$ and b units of $(C_3H_6O)$ may be present in any order. The ethoxylate group or the propoxylate group may be in any order; preferably the value of a is greater than the value of b, more preferably the value of a is greater than 2.5 times, preferably 5 times, or more preferably 9 times the value of b.

The value of a+b of the alkoxylated phenol is also known as a degree of alkoxylation of the alkoxylated phenol. It will be appreciated that the alkoxylated phenol may be a mixture of compounds, wherein one or more compounds has a structure according to Formula (I). Further, at least two, preferably at least three, more preferably at least four, even more preferably at least five compounds of the mixture of compounds may each have a structure according to Formula (I) and comprise at least 5% by the total weight of the mixture of compounds. It will be appreciated by a skilled person that Gas Chromatography/Mass Spectrometry (GC/MS) methods may be used to determine the individual ethoxylate or propoxylate species in an alkoxylated phenol.

The alkoxylated phenol may be selected from the group consisting of: ethoxylated phenol, ethoxylated-propoxylated phenol and combinations thereof, preferably ethoxylated phenol. Accordingly, the reaction of ethylene oxide with a phenol containing compound results in ethoxylated phenol as shown in the following reaction:
$ROH + C_2H_4O \rightarrow ROCH_2CH_2OH$, wherein ROH is phenol containing compound.
Similarly, the reaction of propylene oxide with a phenol containing compound results in propoxylated phenol as shown in the following reaction:
$ROH + n\ OCH_2CHCH_3 \rightarrow R(OCH_2CHCH_3)_nOH$, wherein ROH is phenol containing compound. Ethoxylation and propoxylation of phenol containing compounds may be performed according to known processes.

The alkoxylated phenol may be in an amount of at least 0.0015%, from 0.0015% to 9%, from 0.05% to 7%, from 0.075% to 5%, from 0.1% to 3% or different combinations of the upper and lower percentages described above or combinations of any integer in the ranges listed above by weight of the freshening composition.

In the following description, the alkoxylated phenol described is ethoxylated phenol. However, it is contemplated that other alkoxylated phenols may be configured for solubilizing the PRMs described hereinafter as long as the alkoxylated phenol is soluble in water and solubilizes the PRMs in water.

The ethoxylated phenol may comprise a structure according to Formula (II):

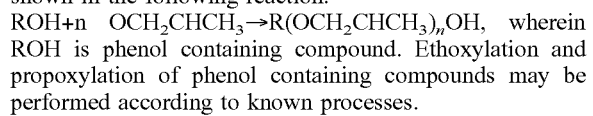

wherein an average value of c, degree of ethoxylation is $3 \leq c \leq 15$, preferably from $4 \leq c \leq 11$, more preferably from $5 \leq c \leq 7$.

Referring to Formula II, "c" is a numerical value corresponding to a number of ethoxylates in the ethoxylated phenol and defines the ethoxylate chain of the ethoxylated phenol, also known as the degree of ethoxylation. Accordingly, an average value of c refers to an average degree of ethoxylation. Without wishing to be bound by theory, the ethoxylated phenol for the freshening composition according to the present invention may have different ethoxylates having ethoxylate chains of differing lengths to meet different freshening product specifications in order to be both water-soluble and oil-soluble in a freshening composition which has a high level of water and a perfume composition having at least 60% of PRMs having a ClogP >1.

Ethoxylated phenols commercially available from Dow under the commercial names of Dowanol™ Glycol Ethers are set out in Table 1 below. As shown in the data described hereinafter in the Examples, use of ethoxylated phenols in which an average value of c is from 4 to 15 results in a clear composition (see Example I) relative to comparative ethoxylated phenols in an average value of c is from 1 to 2.

TABLE 1

| | Commercial Name | | |
|---|---|---|---|
| | DOWANOL EPh Glycol Ether | DOWANOL DiEPh | DOWANOL EPh6 Glycol Ether |
| | | Chemical Nomenclature | |
| Physical Property (Units) | Ethylene glycol phenyl ether | Diethylene glycol phenyl ether | Hexaethylene glycol phenyl ether |
| Molecular Weight (g/mol) | 138.2 | 182.2 | 358/4 |
| Boiling point (° C. @ 760 mmHg) | 244 | 282 | >350 |
| Flash Point (° C.) | 121 | 138 | >149 |
| Evaporation Rate (nBuAc = 1) | 0.001 | 0.0002 | <0.0001 |
| Specific Gravity at 25/25° C. | 1.109 | 1.112 | 1.12 |
| Density (g/cc at 25° C.) | 1.106 | 1.109 | 1.120 |
| Viscosity (cP at 25° C.) | 21.5 | 30 | 89-93 |
| Vapor Pressure (mm Hg at 20° C.) | 0.004 | <0.002 | <0.0001 |
| Surface Tension (dynes/cm) | 42.0 | 37.7 | 45.2 |
| Hansens Solubility Parameters (joules/cm$^3$)$^{1/2}$ | | | |
| delta d | 17.8 | 16.4 | 17.4 |
| delta p | 5.7 | 6.7 | 6.6 |
| delta h | 14.3 | 11.6 | 10.6 |
| Solubility (wt % at 25° C. In Water) | 2.5 | 4.00 | Infinity |
| Solubility (wt % at 25° C. Water In) | 9.0 | 22 | Infinity |

C. Perfume Composition (Hereinafter "Perfume")

The freshening composition comprises a perfume formulated in an effective amount such that it provides a desired scent characteristic and can be homogenously solubilized in the freshening composition to deliver a consistent release profile. The perfume comprises at least 60% by weight of the perfume of Perfume Raw Materials (PRMs) having a ClogP value greater than 1.0. The perfume may be in an amount of at least 0.001%, from 0.002% to 3%, from 0.005% to 1%, from 0.005% to 0.4%, or different combinations of the upper and lower percentages described above or combinations of any integer in the ranges listed above by weight of the freshening composition. The total weight ratio of the ethoxylated phenol to the perfume may be from 0.1:1 to 9,000:1, from 0.1:1 to 500:1, 0.15:1 to 20:1 or different combinations of the upper and lower weight ratios described above or combinations of any integer in the ranges listed above. Inventive Samples comprising ethoxylated phenols with the perfume in Table 15 of Example IV show improved turbidity results relative to the Comparative Samples which will be described hereinafter in Example IV.

The PRMs may be defined by their boiling point ("B.P.") and octanol/water partition coefficient ("P"). The boiling point referred to herein is measured under normal standard pressure of 760 mmHg. The boiling points of many PRMs, at standard 760 mm Hg, are outlined in "Perfume and Flavor Chemicals (Aroma Chemicals)," written and published by Steffen Arctander, 1969.

The ClogP values may be defined by four groups and the PRMs may be selected from one or more of these ClogP groups. The first group comprises PRMs that have a B.P. of about 250° C. or less and ClogP of about 3 or less. Exemplary PRMs of the first group include, but are not limited to, PRMs as shown in Table 2 below.

TABLE 2

Examples of First Group of PRMs

| Perfume Raw Material (PRM) Name | IUPAC Name | CAS Number | Boiling Point, BP (° C.) | ClogP |
|---|---|---|---|---|
| Allyl Caproate | prop-2-enyl hexanoate | 128-68-2 | 185 | 2.772 |
| Amyl Acetate | pentyl acetate | 628-63-7 | 142 | 2.258 |
| Amyl Propionate | pentyl propanoate | 624-54-4 | 161 | 2.657 |
| Anisic Aldehyde | 4-methoxybenzaldehyde | 123-11-5 | 248 | 1.779 |
| Anisole | Anisole | 100-66-3 | 154 | 2.061 |
| Benzaldehyde | Benzaldehyde | 100-52-7 | 179 | 1.48 |
| Benzyl Acetate | Benzyl Acetate | 140-11-4 | 215 | 1.96 |
| Benzyl Acetone | 4-phenylbutan-2-one | 2550-26-7 | 235 | 1.739 |
| Benzyl Alcohol | phenylmethanol | 100-51-6 | 205 | 1.1 |
| Benzyl Formate | Benzyl Formate | 104-57-4 | 202 | 1.414 |
| Benzyl IsoValerate | 2-phenylethyl 3-methylbutanoate | 140-26-1 | 246 | 2.887 |
| Benzyl Propionate | Benzyl Propionate | 122-63-4 | 222 | 2.489 |
| Beta Gamma Hexenol | (Z)-hex-3-en-1-ol | 928-96-1 | 157 | 1.337 |
| Camphor Gum | (1R,4S)-1,7,7-trimethylbicyclo[2.2,1]heptan-2-one | 464-48-2 | 208 | 2.117 |
| laevo-Carveol | 2-methyl-5-prop-1-en-2-ylcyclohex-2-en-1-ol | 99-48-9 | 227 | 2.265 |
| d-Carvone | (5S)-2-methyl-5-prop-1-en-2-ylcyclohex-2-en-1-one | 2244-16-8 | 231 | 2.01 |
| laevo-Carvone | (5R)-2-methyl-5-prop-1-en-2-ylcyclohex-2-en-1-one | 6485-40-1 | 230 | 2.203 |
| Cinnamyl Formate | [(E)3-phenylprop-2-enyl] formate | 104-65-4 | 250 | 1.908 |
| Cis-Jasmone | 3-methyl-2-[(Z)-pent-2-enyl]cyclopent-2-en-1-one | 488-10-8 | 248 | 2.712 |
| Cis-3-Hexenyl Acetate | [(Z)-hex-3-enyl] acetate | 3681-71-8 | 169 | 2.243 |
| Cis-6-Nonen-1-OL FCC | (Z)-non-6-en-1-ol | 35854-86-5 | 214.2 | 2.52 |
| Cuminic alcohol | (4-propan-2-ylphenyl)methanol | 536-60-7 | 248 | 2.531 |
| Cuminic aldehyde | 4-propan-ylbenzaldehyde | 122-03-2 | 236 | 2.78 |
| Cyclal C | 3,5-dimethylcyclohex-3-ene-1-carbaldehyde | 68039-48-5 | 180 | 2.301 |
| Dimethyl Benzyl Carbinol | 2-methyl-1-phenylpropan-2-ol | 100-86-7 | 215 | 1.891 |
| Dimethyl Benzyl Carbinyl Acetate | (2-methyl-1-phenylpropan-2-yl) acetate | 151-05-3 | 250 | 2.797 |
| Ethyl Acetate | Ethyl Acetate | 141-78-6 | 77 | 0.73 |
| Ethyl Benzoate | Ethyl Benzoate | 93-89-0 | 212 | 2.64 |
| Ethyl Hexyl Ketone | nonan-3-one | 925-78-0 | 190 | 2.916 |
| Ethyl-2-methyl butyrate | ethyl 2-methylbutanoate | 7452-79-1 | 131 | 2.1 |
| Ethyl-2-Methyl Pentanoate | ethyl 2-methylpentanoate | 39255-32-8 | 143 | 2.7 |
| Ethyl Phenyl Acetate | ethyl 2-phenylacetate | 101-97-3 | 229 | 2.489 |
| Eucalyptol | 1,3,3-trimethyl-2-oxabicyclo[2.2.2]octane | 470-82-6 | 176 | 2.756 |
| Fenchyl Alcohol | 1,3,3-trimethylbicyclo[2.2.1]heptan-2-ol | 1632-73-1 | 200 | 2.579 |
| Hexyl Acetate | Hexyl Acetate | 142-92-7 | 172 | 2.787 |
| Hexyl Acetate | Hexyl Formate | 629-33-4 | 155 | 2.381 |
| Hydratropic Alcohol | 2phenylpropanl-ol | 1123-85-9 | 219 | 1.582 |
| Hydroxycitronellal | 7-hydroxy-3,7-dimethyloctanal | 107-75-5 | 241 | 1.541 |
| Isoamyl Alcohol | 3-methylbutan-1-ol | 123-51-3 | 132 | 1.222 |
| Isomenthone | 5-methyl-2-propan-2-ylcyclohexan-1-one | 89-80-5 | 210 | 2.831 |
| Isopulegyl Acetate | (5-methyl-2-prop-1-en-2-ylcyclohexyl) acetate | 89-49-6 | 239 | 2.1 |
| Isoquinoline | Isoquinoline | 119-65-3 | 243 | 2.08 |
| Ligustral | 2,4-dimethylcyclohex-3-ene-1-carbaldehyde | 68039-49-6 | 177 | 2.301 |

TABLE 2-continued

Examples of First Group of PRMs

| Perfume Raw Material (PRM) Name | IUPAC Name | CAS Number | Boiling Point, BP (° C.) | ClogP |
|---|---|---|---|---|
| Linalool | 3,7-dimethylocta-1,6-dien-3-ol | 78-70-6 | 198 | 2.429 |
| Linalyl Formate | 3,7-dimethylocta-1,6-dien-3-yl formate | 115-99-1 | 202 | 2.929 |
| Menthone | 5,5-dimethylcyclohexane-1,3-dione | 126-81-8 | 207 | 2.65 |
| Methyl Amyl Ketone | heptan-2-one | 110-43-0 | 152 | 1.848 |
| Methyl Anthranilate | methyl 2-aminobenzoate | 134-20-3 | 237 | 2.024 |
| Methyl Benzoate | Methyl Benzoate | 93-58-3 | 200 | 2.111 |
| Methyl Eugenol | 1,2-dimethoxy-4-prop-2-enylbenzene | 93-15-2 | 249 | 2.783 |
| Methyl Heptenone | 6-methylhept-5-en-2-one | 110-93-0 | 174 | 1.703 |
| Methyl Heptine Carbonate | methyl oct-2-ynoate | 111-12-6 | 217 | 2.528 |
| Methyl Heptyl Ketone | nonan-2-one | 821-55-6 | 194 | 1.823 |
| Methyl Hexyl Ketone | octan-2-one | 111-13-7 | 173 | 2.377 |
| Methyl Phenyl Carbinyl Acetate | 1-phenylethyl acetate | 93-92-5 | 214 | 2.269 |
| Nerol | (2Z)-3,7-dimethylocta-2,6-dien-1-ol | 106-25-2 | 227 | 2.649 |
| OCTAHYDRO COUMARIN | octahydro-2H-chromen-2-one | 4430-31-3 | 222.9 | 1.58 |
| Octyl Alcohol (Octanol-2) | octan-2-ol | 123-96-6 | 179 | 2.719 |
| para-Methyl Acetophenone | 1-(4-methylphenyl)ethene | 122-00-9 | 228 | 2.08 |
| Phenoxy Ethanol | 1-phenoxyethanol | 56101-99-6 | 245 | 1.188 |
| Phenyl Acetaldehyde | 2-phenylacetaldehyde | 122-78-1 | 195 | 1.78 |
| Phenyl Acetaldehyde Dimethyl Acetal | (2,2-dimethoxyethyl)benzene | | 249.5 | 2.15 |
| Phenyl Ethyl Acetate | 2,2-dimethoxyethylbenzene | 101-48-4 | 232 | 2.129 |
| Phenyl Ethyl Alcohol | 2-phenylethanol | 60-12-8 | 220 | 1.183 |
| Phenyl Ethyl Dimethyl Carbinol | 2-methyl-4-phenylbutan-2-ol | 103-05-9 | 238 | 2.42 |
| Prenyl Acetate | 3-methylbut-2-enyl-acetate | 1191-16-8 | 155 | 1.684 |
| Propyl Butyrate | propyl butanoate | 105-66-8 | 143 | 2.21 |
| Pulegone | 5-methyl-2-propan-2-ylidenecyclohexan-1-one | 15932-80-6 | 224 | 2.35 |
| Rose Oxide | 4-methyl-2-(2-methylprop-1-enyl)oxane | 16409-43-1 | 182 | 2.896 |
| 4-Terpinenol | 4-methyl-1-propan-2-ylcyclohex-3-en-1-ol | 562-74-3 | 212 | 2.749 |
| alpha-Terpineol | 2-(4-methylcyclohex-3-en-1-yl)propan-2-ol | 98-55-5 | 219 | 2.569 |
| Viridine | 2,2-dimethoxyethylbenzene | 101-48-4 | 221 | 1.293 |
| Violiff | (Z)-cyclooct-4-en-1-yl methyl carbonate | 87731-18-8 | 214.4 | 2.79 |

The second group comprises PRMs that have a B.P. of 250° C. or less and ClogP of 3.0 or more. Exemplary PRMs of the second group which may be used include, but are not limited to, PRMs as shown in Table 3 below.

TABLE 3

Examples of Second Group of PRMs

| Perfume Raw Material (PRM) Name | IUPAC Name | CAS No. | Boiling Point, BP (° C.) | ClogP |
|---|---|---|---|---|
| allo-Ocimene | (4E,6E-2,6-dimethylocta-2,4,6-triene | 673-84-7 | 192 | 4.362 |
| Anethol | 1-methoxy-4-[(E)-prop-1-enyl]benzene | 104-46-1 | 236 | 3.314 |

TABLE 3-continued

Examples of Second Group of PRMs

| Perfume Raw Material (PRM) Name | IUPAC Name | CAS No. | Boiling Point, BP (° C.) | ClogP |
|---|---|---|---|---|
| Benzyl Butyrate | benzyl butanoate | 103-37-7 | 240 | 3.698 |
| Camphene | 2,2-dimethyl-3-methylidenebicyclo[2.2.1]heptane | 79-92-5 | 159 | 4.192 |
| Carvacrol | 2-methyl-5-propan-2-ylphenol | 499-75-2 | 238 | 3.401 |
| cis-3-Hexenyl Tiglate | [(Z)-hex-3-enyl] (E)-2-methylbut-2-enoate | 67883-79-8 | 101 | 3.7 |
| cis Ocimene | (E)-3,7-dimethylocta-1,3,6-triene | — | 156.7 | 4.26 |
| CITRAL DIMETHYL ACETAL | (E)-1,1-dimethoxy-3,7-dimethylocta-2,6-diene | 7549-37-3 | 235.6 | 3.61 |
| Citral (Neral) | (2E-3,7-dimethylocta-2,6- dienal | 5392-40-5 | 228 | 3.12 |
| Citronellol | 3,7-dimethyloct-6-en-1-ol | 106-22-9 | 225 | 3.193 |
| Citronellyl Acetate | 3,7-dimethyloct-6-enyl acetate | 150-84-5 | 229 | 3.67 |
| Citronellyl Isobutyrate | 3,7-dimethyloct-6-enyl 2-methylpropanoate | 97-89-2 | 249 | 4.937 |
| Citronellyl Nitrile | 3,7dimethyloct-6-enenitrile | 51566-62-2 | 225 | 3.094 |
| Cyclohexyl Ethyl Acetate | 2-cyclohexylethyl acetate | 21722-83-8 | 187 | 3.321 |
| Decyl Aldehyde | Decanal | 112-31-2 | 209 | 4.008 |
| DECENAL (TRANS-4) | (E)-dec-4-enal | 30390-50-2 | 214.7 | 3.60 |
| Dihydro Myrcenol | 2-methyl-6-methylideneoctan-2-ol | 18479-59-9 | 208 | 3.03 |
| Fenchyl Acetate | (1,3,3-trimethyl-2-bicyclo[2.2.1]heptanyl) acetate | 4057-31-2 | 220 | 3.485 |
| gamma Methyl Ionone | (Z)-3-methyl-4-(2,6,6-trimethylcyclohex-2-en-1-yl)but-3-en-2-one | 127-51-5 | 230 | 4.089 |
| gamma-Nonalactone | 5-pentyloxolan-2-one | 104-61-0 | 243 | 3.14 |
| Geraniol | (E)-3,7-dimethylocta-2,6-dien-1-ol | 106-24-1 | 224.8 | 3.41 |
| Geranyl Acetate | [(2E)-3,7-dimethylocta-2,6-dienyl] acetate | 105-87-3 | 245 | 3.715 |
| Geranyl Formate | [(2E)-3,7-dimethylocta-2,6-dienyl] formate | 105-86-2 | 216 | 3.269 |
| Geranyl Isobutyrate | [(2E)-3,7-dimethylocta-2,6-dienyl] 2-methylpropanoate | 2345-26-8 | 245 | 4.393 |
| Geranyl Nitrile | (2E)-3,7-dimethylocta-2,6-dienenitrile | 5146-66-7 | 222 | 3.139 |
| Hexyl Neopentanoate | hexyl 2,2-dimethylpropanoate | 5434-57-1 | 224 | 4.374 |
| Hexyl Tiglate | hexyl (E)-2-methylbut-2-enoate | 16930-96-4 | 231 | 3.8 |
| alpha-Ionone | (E)-4-(2,6,6-trimethylcyclohex-2-en-1-yl)but-3-en-2-one | 127-41-3 | 237 | 3.381 |
| beta-Ionone | (E)-4-(2,6,6-trimethylcyclohexen-1-yl)but-3-en-2-one | 14901-07-6 | 239 | 3.96 |
| gamma-Ionone | (E-4-(2,2-dimethyl-6-methylidenecyclohexyl)but-3-en-2-one | 79-76-5 | 240 | 3.78 |
| alpha-Irone | (E)4-(2,5,6,6-tetramethylcyclohex-2-en-1-yl)but-3-en-2-one | 79-69-6 | 250 | 3.82 |
| Isobornyl Acetate | (1,7,7-trimethyl-2-bicyclo[2.2.1]heptanyl) acetate | 76-49-3 | 227 | 3.485 |
| Isobutyl Benzoate | 2-methylpropyl benzoate | 120-50-3 | 242 | 3.028 |
| Isononyl Acetate | 3,5,5-trimethylhexyl acetate | 58430-94-7 | 177.7 | 3.46 |
| Isononyl Alcohol | 7-methyloctan-1-ol | 2430-22-0 | 194 | 3.078 |
| Isopulegol | (1R,2S,5R)-5-methyl-2-prop-1-en-2-ylcyclohexan-1-ol | 89-79-2 | 212 | 3.33 |
| Lauric Aldehyde | Dodecanal | 112-54-9 | 249 | 5.066 |
| d-Limonene | (4R)-1-methyl-4-prop-1-en-2-ylcyclohexene | 5989-27-5 | 177 | 4.232 |
| Linalyl Acetate | 3,7-dimethylocta-1,6-dien-3-yl acetate | 115-95-7 | 220 | 3.5 |
| 7-Methyloctyl acetate | 7-methyloctyl acetate | 40379-24-6 | 208.8 | 4.25 |
| Menthyl Acetate | (5-methyl-2-propan-2-ylcyclohexyl) acetate | 2230-87-7 | 227 | 3.21 |
| Methyl Chavicol | 1-methoxy-4-prop-2-enylbenzene | 140-67-0 | 216 | 3.074 |
| Methyl Nonyl Acetaldehyde | 2-methylundecanal | 110-41-8 | 232 | 4.846 |
| Myrcene | 7-methyl-3-methylideneocta-1,6-diene | 123-35-3 | 167 | 4.272 |
| Neral | (2Z)-3,7-dimethylocta-2,6-dienal | 5392-40-5 | 228 | 3.12 |

TABLE 3-continued

Examples of Second Group of PRMs

| Perfume Raw Material (PRM) Name | IUPAC Name | CAS No. | Boiling Point, BP (° C.) | ClogP |
|---|---|---|---|---|
| Neryl Acetate | [(2Z)-3,7-dimethylocta-2,6-dienyl] acetate | 141-12-8 | 231 | 3.555 |
| Nonyl Acetate | nonyl acetate | 143-13-5 | 212 | 4.374 |
| Nonyl Aldehyde | nonanal | 124-19-6 | 212 | 3.479 |
| OCIMENE | (Z)-3,7-dimethylocta-1,3,6-triene | 3338-55-4 | 156.7 | 4.26 |
| Orange Terpenes (d-Limonene) | (4R)-1-methyl-4-prop-1-en-2-ylcyclohexene | 5989-27-5 | 177 | 4.232 |
| para-Cymene | 1-methyl-4-propan-2-ylbenzene | 99-87-6 | 179 | 4.068 |
| Phenyl Ethyl Isobutyrate | ethyl 2-methyl-2-phenylpropanoate | 2901-13-5 | 250 | 3 |
| alpha-Pinene | 2,6,6-trimethylbicyclo[3.1.1]hept-2-ene | 80-56-8 | 157 | 4.122 |
| beta-Pinene | 6,6-dimethyl-2-methylidenebicyclo[3.1.1]heptane | 25719-60-2 | 166 | 4.182 |
| gamma-Terpinene | 1-methyl-4-propan-2-ylcyclohexa-1,4-diene | 99-85-4 | 183 | 4.232 |
| Terpinolene | 1-methyl-4-propan-2-ylidenecyclohexene | 586-62-9 | 184 | 4.232 |
| Terpinyl acetate | 2-(4-methylcyclohex-3-en-1-yl)propan-2-yl acetate | 80-26-2 | 223.7 | 3.91 |
| Tetrahydro Linalool | 3,7-dimethyloctan-3-ol | 78-69-3 | 191 | 3.517 |
| Tetrahydro Myrcenol | 2,6-dimethyloctan-2-ol | 18479-57-7 | 208 | 3.517 |
| Undecenal | undec-2-enal | 1337-83-3 | 223 | 4.053 |
| undecyl aldehyde | undecanal | 112-44-7 | 234.4 | 4.62 |
| undecylenic aldehyde | undec-10-enal | 112-45-8 | 239.1 | 3.97 |
| Veratrol | 1,2-dimethoxybenzene | 91-16-7 | 206 | 3.14 |
| Verdox | (2-tert-butylcyclohexyl) acetate | 88-41-5 | 221 | 4.059 |
| Vertenex | (4-tert-butylcyclohexyl) acetate | 1900-69-2 | 232 | 4.06 |

The third group comprises PRMs that have a B.P. of 250° C. or more and ClogP of 3.0 or less. The fourth group comprises PRMs that have a B.P. of 250° C. or more and ClogP of 3.0 or more. Exemplary PRMs of the third and fourth groups which may be used include, but are not limited to, PRMs as shown in Table 4 below. The freshening composition may comprise any combination of PRMs from one or more of the first, second, third and fourth groups.

TABLE 4

Examples of Third and Fourth Groups of PRMs

| Perfume Raw Material (PRM) Name | IUPAC Name | CAS No. | Boiling Point BP (° C.) | ClogP |
|---|---|---|---|---|
| Amber Xtreme | 2,2,6,6,7,8,8-heptamethyldecahydro-2H-indeno[4,5-b]furan | 476332-65-7 | 306.5 | 6.14 |
| Amyl Benzoate | pentyl benzoate | 2049-96-9 | 262 | 3.417 |
| Amyl Cinnamate | pentyl (E)-3-phenylprop-2-enoate | 3487-99-8 | 310 | 3.771 |
| Amyl Cinnamic Aldehyde | [(E)-2-[bis[(2E-3,7-dimethylocta-2,6-dienoxy]methyl]hept-1-enyl]benzene | 67785-69-7 | 285 | 4.324 |
| iso-Amyl Salicylate | 3-methylbutyl 2-hydroxybenzoate | 87-20-7 | 277 | 4.601 |
| Aurantiol | methyl 2[(7-hydroxy-3,7-dimethyloctylidene)amino]benzoate | 89-43-0 | 450 | 4.216 |
| Benzophenone | diphenylmethanone | 119-61-9 | 306 | 3.12 |
| Benzyl Salicylate | benzyl 2-hydroxybenzoate | 118-58-1 | 300 | 4.383 |
| CARYOPHYLLENE OXIDE | (1R,4R,6R,10S)-4,12,12-trimethyl-9-methylene-5-oxatricyclo[8.2.0.04,6]dodecane | 1139-30-6 | 270.6 | 4.47 |
| Cadinene | (1S,4S,4aS,6R,8aR)-1,6-dimethyl-4-propan-2-yl-1,2,3,4,4a,5,6,8a-octahydronaphthalene | 880143-55-5 | 275 | 7.346 |
| Cedrol | (1S,2R,5S,7R,8R)-2,6,6,8-tetramethyltricyclo[5.3.1.0$^{1,5}$]undecan-8-ol | 77-53-2 | 291 | 4.53 |
| Cedryl Acetate | [(1S,2R,8R)-2,6,6,8-tetramethyl-8-tricyclo[5.3.1.0$^{1,5}$]undecanyl] acetate | — | 303 | 5.436 |
| Cedryl Methyl Ether | (3R,3aR,6S,7S,8aS)-6-methoxy-3,6,8,8-tetramethyloctahydro-1H-3a,7-methanoazulene | 67874-81-1 | 301.8 | 5.08 |

TABLE 4-continued

Examples of Third and Fourth Groups of PRMs

| Perfume Raw Material (PRM) Name | IUPAC Name | CAS No. | Boiling Point BP (° C.) | ClogP |
|---|---|---|---|---|
| CORAMBER | 1-((2-(tert-butyl)cyclohexyl)oxy)butan-2-ol | — | 304.9 | 4.03 |
| 5-CYCLOHEXADECEN-1-ONE | (E)-cyclohexadec-5-en-1-one | 37609-25-9 | 331 | 5.17 |
| Cyclohexyl Salicylate | cyclohexyl 2-hydroxybenzoate | 25485-88-5 | 304 | 5.265 |
| Cyclamen Aldehyde | 2-methyl-3-(4-propan-2-ylphenyl)propanal | 103-95-7 | 270 | 3.68 |
| Dihydro Isojasmonate | methyl 2-hexyl-3-oxocyclopentane-1-carboxylate | 37172-53-5 | 300 | 3.009 |
| Diphenyl Methane | benzylbenzene | 101-81-5 | 262 | 4.059 |
| DIPHENYL OXIDE | phenoxybenzene | 101-84-8 | 267.8 | 4.03 |
| Ethylene Brassylate | 1,4-dioxacycloheptadecane-5,17-dione | 105-95-3 | 332 | 4.554 |
| ethyl laurate | ethyl dodecanoate | 106-33-2 | 264.4 | 5.81 |
| Ethyl Methyl Phenyl Glycidate | ethyl 3-methyl-3-phenyloxirane-2-carboxylate | 77-83-8 | 260 | 3.165 |
| Ethyl Undecylenate | ethyl undec-10-enoate | 692-86-4 | 264 | 4.888 |
| iso-Eugenol | 2-methoxy-4-[(E)-prrop-1-enyl]phenol | 97-54-1 | 266 | 2.547 |
| Exaltolide | oxacyclohexadecan-2-one | 106-02-5 | 280 | 5.346 |
| Farnesol | (2E,6E)-3,7,11-trimethyldodeca-2,6,10-trien-1-ol | 4602-84-0 | 306.1 | 4.72 |
| FRUTENE | 3a,4,5,6,7,7a-hexahydro-1H-4,7-methanoinden-6-yl propionate | — | 294 | 2.32 |
| Galaxolide | 4,6,6,7,8,8-hexamethyl-1,3,4,7-tetrahydrocyclopenta[g]isochromene | 1222-05-5 | 260 | 5.482 |
| Geranyl Anthranilate | [(2E)-3,7-dimethylocta-2,6-dienyl] 2-aminobenzoate | 67859-99-8 | 312 | 4.216 |
| GLYCOLIERRAL | 2-[1S,4R)-7-rnethyl-5-propan-2-yl-2-bicyclo[2.2.2]octanyl]-1,3-dioxolane | — | 331.3 | 3.81 |
| Hexadecanolide | oxacycloheptadecan-2-one | 109-29-5 | 294 | 6.805 |
| HEXAROSE | [(2E)-3,7-dimethylocta-2,6-dienyl] hexadecanoate | 3681-73-0 | 333.3 | 10.75 |
| Hexyl Cinnamic Aldehyde | (2E)-2-benzylideneoctanal | 165184-98-5 | 305 | 5.473 |
| Hexyl Salicylate | hexyl 2-hydroxybenzoae | 6259-76-3 | 290 | 5.26 |
| Iso E Super Or Wood | 1-((2S,3S)-2,3,8,8-tetramethyl-1,2,3,4,5,6,7,8-octahydronaphthalen-2-yl)ethan-1-one | 54464-57-2 | 325.3 | 4.72 |
| Isolongifolanone | 1,1,5,5-tetramethylhexahydro-2H-2,4a-methanonaphthalen-8(5H)-one | 23787-90-8 | 323.2 | 4.09 |
| Lauryl alcohol, ≥98% | dodecan-1-ol | 112-53-8 | 269.8 | 5 |
| Linalyl Benzoate | 3,7-dimethylocta-1,6-dien-3-yl benzoate | 126-64-7 | 263 | 5.233 |
| Lyral | 4-(4-hydroxy-4-methylpentyl)cyclohex-3-ene-1-carbaldehyde | 31906-04-4 | 324 | 2.85 |
| 2-Methoxy Naphthalene | 2-methoxynaphthalene | 93-04-9 | 275 | 3.235 |
| Methyl Cinnamate | methyl (E)-3-phenylprop-2-enoate | 103-26-4 | 263 | 2.62 |
| Methyl Dihydrojasmonate | methyl 2-[(1R,2R)-3-oxo-2-pentylcyclopentyl]acetate | 2630-39-9 | 300 | 2.275 |
| beta-Methyl Naphthyl ketone | 1-naphthalen-2-ylethanone | 93-08-3 | 300 | 2.275 |
| MAGNOLAN | 2,4-dimethyl-4,4a,5,9b-tetrahydroindeno[1,2-d][1,3]dioxine | 27606-09-3 | 340 | 2.99 |
| MAJANTOL | 2,2-dimethyl-3-(m-tolyl)propan-1-ol | 103694-68-4 | 281.3 | 3.04 |
| Musk Ketone | 1-(4-tert-butyl-2,6-dimethyl-3,5-dinitrophenyl)ethanone | 81-14-1 | M.P.[1] = 137 | 3.014 |
| Musk Tibetine | 1-tert-butyl-3,4,5-trimethyl-1-2,6-dinitrobenzene | 145-39-1 | M.P. = 136 | 3.831 |
| Myristicin | 4-methoxy-6-prop-2-enyl-1,3-benzodioxole | 607-91-0 | 276 | 3.2 |
| delta-Nonalactone | 6-butyloxan-2-one | 3301-94-8 | 280 | 2.76 |
| Oxyoctaline Formate | 2,4a,5,8a-tetramethyl-1,2,3,4,4a,7,8,8a-octahydronaphthalen-1-yl formate | | 298 | 4.69 |
| Patchouli Alcohol | (1R,3R,6S,7S,8S)-2,2,6,8-tetramethyltricyclo[5.3.1.0$^{3,8}$]undecan-3-ol | 5986-55-0 | 285 | 4.53 |
| Phantolide | 1-(1,1,2,3,6-hexamethyl-2H--inden-5-yl)ethanone | 15323-35-0 | 288 | 5.977 |
| PHENYL HEXANOL | 3-methyl-5-phenylpentan-1-ol | 4471-05-0 | 287.0 | 2.96 |
| Thibetolide | oxacyclohexadeca-2-one | 106-02-5 | 280 | 6.246 |
| delta-Undecalactone | 6-hexyloxan-2-one | 710-04-3 | 290 | 3.83 |

TABLE 4-continued

Examples of Third and Fourth Groups of PRMs

| Perfume Raw Material (PRM) Name | IUPAC Name | CAS No. | Boiling Point BP (° C.) | ClogP |
|---|---|---|---|---|
| gamma-Undecalactone | 5-heptyloxolan-2-one | 104-67-6 | 297 | 4.14 |
| Vanillin | 4-hydroxy-3-methoxybenzaldehyde | 121-33-5 | 285 | 1.58 |
| Vetiveryl Acetate | (4,8-dimethyl-2-propan-2-ylidene-3,3a,4,5,6,8a-hexahydro-1H-azulen-6-yl) acetate | 117-98-6 | 285 | 4.882 |
| Yara-Yara | 2-methoxynaphthalene | 93-04-9 | 274 | 3.235 |

Wherein the ethoxylated phenol has an average c value from 5 to 7, the perfume composition may comprise at least 80%, from 80% to 100%, from 80% to 100%, from 90% to 100%, by weight of the perfume composition of PRMs having a ClogP greater than 2.0, at least 2.5, more preferably greater than 3.0, even more preferably greater than 3.5; preferably weighted average ClogP for the perfume is from 2.5 to 6.0, more preferably from 3.5 to 6.0. Perfume raw materials which may be used include, but are not limited to, exemplary perfume raw materials as shown in Table 5 below.

TABLE 5

| Perfume Raw Material (PRM) | CAS | ClogP |
|---|---|---|
| Ligustral Or Triplal | 68039-49-6 | 2.98 |
| Citronellol | 106-22-9 | 3.56 |
| HYDROXYCITRONELLAL | 107-75-5 | 2.08 |
| Linalool | 78-70-6 | 3.29 |
| Methyl Phenyl Carbinyl Acetate | 93-92-5 | 2.38 |
| Pyranol | 63500-71-0 | 2.31 |
| Ethyl Maltol | 4940-11-8 | 0.5 |
| Ethyl Vanillin | 121-32-4 | 1.59 |
| Benzyl acetate | 140-11-4 | 1.94 |
| Helional | 1205-17-0 | 2.03 |
| Cyclo Galbanate | 68901-15-5 | 2.88 |
| 4-tertiary-Butyl cyclohexyl acetate | 32210-23-4 | 4.46 |
| Verdox | 88-41-5 | 4.46 |
| Orange Terpenes | 68647-72-3 | 4.15 |
| UNDECALACTONE | 104-67-6 | 3.18 |
| LINALYL ACETATE | 115-95-7 | 3.92 |
| Hexyl salicylate | 6259-76-3 | 4.85 |
| Habanolide 100% | 111879-80-2 | 4.77 |
| Iso E super | 54464-57-2 | 4.72 |
| Ionone Gamma Methyl | 127-51-5 | 4.22 |
| Ethyl Trimethylcyclopenteene Butenol | 28219-61-6 | 4.38 |

D. Sulfur-Containing Pro-Perfume

The freshening composition may comprise a sulfur-containing pro-perfume. A technical effect of the sulfur-containing pro-perfume is that it improves the stability of freshening compositions. The sulfur-containing pro-perfume compound may be present at various levels in the composition. Specifically, the freshening composition may comprise from about 0.001% to about 5%, alternatively from about 0.001% to about 3%, alternatively from about 0.01% to about 1%, alternatively about 0.01% to about 0.5%, alternatively about 0.01% to about 0.1%, alternatively at least about 0.02%, or different combinations of the upper and lower percentages described above or combinations of any integer in the ranges listed above of a sulfur-containing pro-perfume by weight of the freshening composition.

The sulfur-containing pro-perfume herein may comprise a compound 5 of formula (I):

$$Y—S—G—Q \quad (I)$$

wherein:

(i) Y is a radical selected from the group consisting of (Y-1) to (Y-7) shown herein below, including isomeric forms:

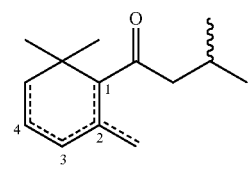
(Y-1)

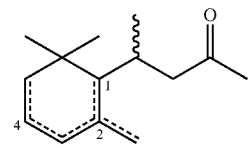
(Y-2)

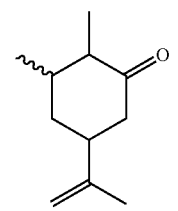
(Y-3)

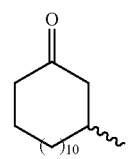
(Y-4)

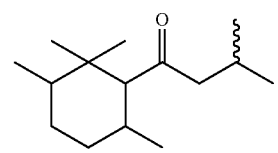
(Y-5)

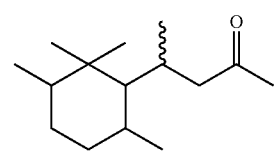
(Y-6)

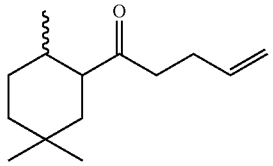

(Y-7)

wherein the wavy lines represent the location of the sulfur (S) bond, and the dotted lines represent a single or double bond;

(ii) G is selected from a divalent or trivalent radical derived from a linear or branched alkyl or alkenyl radical having from 2 to 15 carbon atoms; and (iii) Q is selected from a hydrogen, a —S—Y group, or a —NR2-Y group, wherein Y is independently selected as defined above, and R2 is selected from a hydrogen or a C1-C3 alkyl group G may be a divalent or trivalent radical, preferably a divalent radical derived from a linear or branched alkyl or alkenyl radical having from 2 to 15 carbon atoms, substituted with one or more groups selected from the group consisting of —OR$^1$, —NR$^1{}_2$, —COOR$^1$, R$^1$ groups, and a combination thereof, wherein R$^1$ is selected from a hydrogen or a C$_1$ to C$_6$ alkyl or alkenyl group. Preferably, G is a divalent radical derived from a linear or branched alkyl or alkenyl radical having from 2 to 15 carbon atoms, substituted with at least one —COOR$^1$ group, preferably substituted with a —COOR$^1$ group, wherein R$^1$ is selected from a hydrogen or a C$_1$ to C$_6$ alkyl or alkenyl group. Even more preferably, G is a divalent radical derived from a linear alkyl radical having a —CH$_2$CH(COOR$^1$) group, wherein R$^1$ is a hydrogen or a methyl or ethyl group. G may be a divalent radical derived from a linear alkyl radical having from 8 to 15 carbon atoms which is either substituted or un-substituted.

The sulfur-containing pro-perfume may be a compound of formula (I) wherein Y is selected from Y-1, Y-2 or Y-3 groups as defined above, and G and Q are defined in any one of the above-described examples. The sulfur-containing pro-perfume may be a sulfide.

Preferably, the sulfur-containing pro-perfume is selected from the group consisting of methyl or ethyl 2-(4-oxo-4-(2,6,6-trimethylcyclohex-3-en-1-yl)butan-2-ylamino)-3-(4-oxo-4-(2,6,6-trimethylcyclohex-3-en-1-yl)butan-2-ylthio) propanate, methyl or ethyl 2-(4-oxo-4-(2,6,6-trimethylcyclohex-2-en-1-yl)butan-2-ylamino)-3-(4-oxo-4-(2,6,6-trimethylcyclohex-2-en-lyl)butan-2-ylthio) propanate, methyl or ethyl 2-(2-oxo-4-(2,6,6-trimethylcyclohex-1-en-1-yl)butan-4-ylamino)-3-(2-oxo-4-(2,6,6-trimethylcyclohex-1-en-1-yl)butan-4-ylthio) propanate, methyl or ethyl 2-(2-oxo-4-(2,6,6-trimethylcyclohex-2-en-1-yl)butan-4-ylamino)-3-(2-oxo-4-(2,6,6-trimethylcyclohex-2-en-1-yl)butan-4-ylthio) propanate, 3-(dodecylthio)-1-(2,6,6-trimethylcyclohex-3-en-1-yl)-1-butanone, 3-(dodecylthio)-1-(2,6,6-trimethylcyclohex-2-en-1-yl)-1-butanone, 4-(dodecylthio)-4-(2,6,6-trimethylcyclohex-2-en-1-yl)-2-butanone, 4-(dodecylthio)-4-(2,6,6-trimethylcyclohex-1-en-1-yl)-2-butanone, 2-dodecylsulfanyl-5-methyl-heptan-4-one, 2-cyclohexyl-1-dodecylsulfanyl-hept-6-en-3-one, 3-(dodecylthio)-5-isopropenyl-2-methylcyclohexanone, and a combination thereof. More preferably, the sulfur-containing pro-perfume compound is selected from the group consisting of 3-(dodecylthio)-1-(2,6,6-trimethylcyclohex-3-en-1-yl)-1-butanone, 4-(dodecylthio)-4-(2,6,6-trimethylcyclo- hex-2-enl-yl)-2-butanone, 4-(dodecylthio)-4-(2,6,6-trimethylcyclohex-len-1-yl)-2-butanone and 3-(dodecylthio)-5-isopropenyl-2-methylcyclohexanone, and a combination thereof. 3-(dodecylthio)-1-(2,6,6-trimethyl-cyclohex-3-en-1-yl)-1-butanone is the most preferred sulfur-containing pro-perfume compound, such as Haloscent® D available from Firmenich located in Geneva, Switzerland, and is defined by its CAS No. 543724-31-8 and has a ClogP of 9.51.

The freshening composition may comprise dodecyl thio-damascone having the general structure shown below.

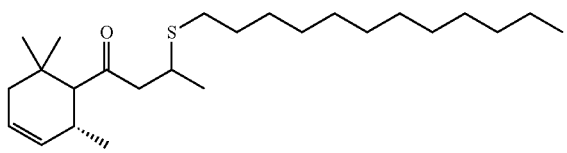 [SMILES: CCCCCCCCCCCCSC(C)CC(=O)C1[C@H](C)C=CCC1(C)C]

Thio-damascone may be present in an amount form about 0.001% to about 1.0%, alternatively from about 0.001% to about 5.0%, alternative from about 0.001% to about 3.0%, alternatively from about 0.01% to about 1.0%, alternatively about 0.01% to about 0.5%, alternative about 0.01% to about 0.1%, alternatively at least about 0.02% by weight of the freshening composition.

The weight ratio of perfume mixture to sulfur-containing pro-perfume may be about 0.01:1 to about 200:1, or about 5:1 to about 50:1, or about 10:1 to about 40:1, or about 10:1 to about 20:1, by weight of the composition.

E. Solvents

The freshening composition may comprise a solvent for solubilizing the perfume. Specifically, the composition may comprise less than 10%, from 0.01% to 5%, from 0.01% to 3%, from 0.01% to 1%, from 0.01% to 0.05%, or different combinations of the upper and lower percentages described above or combinations of any integer in the ranges listed above of a solvent by weight of the freshening composition. The solvent may be selected from a group consisting of: an alcohol, a polyol and mixtures thereof. The solvent may comprise low molecular weight monohydric alcohols (e.g., ethanol, methanol, and isopropanol, or polyols, such as ethylene glycol and propylene glycol).

When the freshening composition is formulated with ethanol together with alkoxylated phenol to define a solvent system, ethanol may be in an amount of less than 10%, less than 5%, less than 3%, from 0.1% to 2% or different combinations of the upper and lower percentages described above or combinations of any integer in the ranges listed above by weight of the freshening composition. Preferably the alkoxylated phenol is ethoxylated phenol.

The freshening composition may be substantially free of a solvent, preferably free of alcohol, more preferably free of ethanol, even more preferably free of a polyol selected from the group consisting of: dipropylene glycol methyl ether, diethylene glycol, 3-methoxy-3-methyl-1-butanol, and mixtures thereof, yet even more preferably free of diethylene glycol.

F. Surfactants

The freshening composition may contain a surfactant to solubilize any excess hydrophobic organic materials, particularly any PRMs, and also optional ingredients (e.g., insect repelling agent, antioxidant, etc.) which can be added to the composition, that are not readily soluble in the composition, to form a clear solution. The freshening composition may comprise less than 3.5%, from 0.01% to 3%, from 0.01% to 1%, from 0.01% to 0.05% or different combinations of the upper and lower percentages described above or combinations of any integer in the ranges listed above of a surfactant by weight of the freshening composition. A suitable surfactant is a no-foaming or low-foaming surfactant. The surfactant may be selected from the group consisting of: nonionic surfactants, cationic surfactants, amphoteric surfactants, zwitterionic surfactants and mixtures thereof. Non-ionic surfactants may further include polyoxy-ethylene castor oil ethers or polyoxyethylene hardened castor oil ethers or mixtures thereof, which are either partially or fully hydrogenated. These ethoxylates have the following formula:

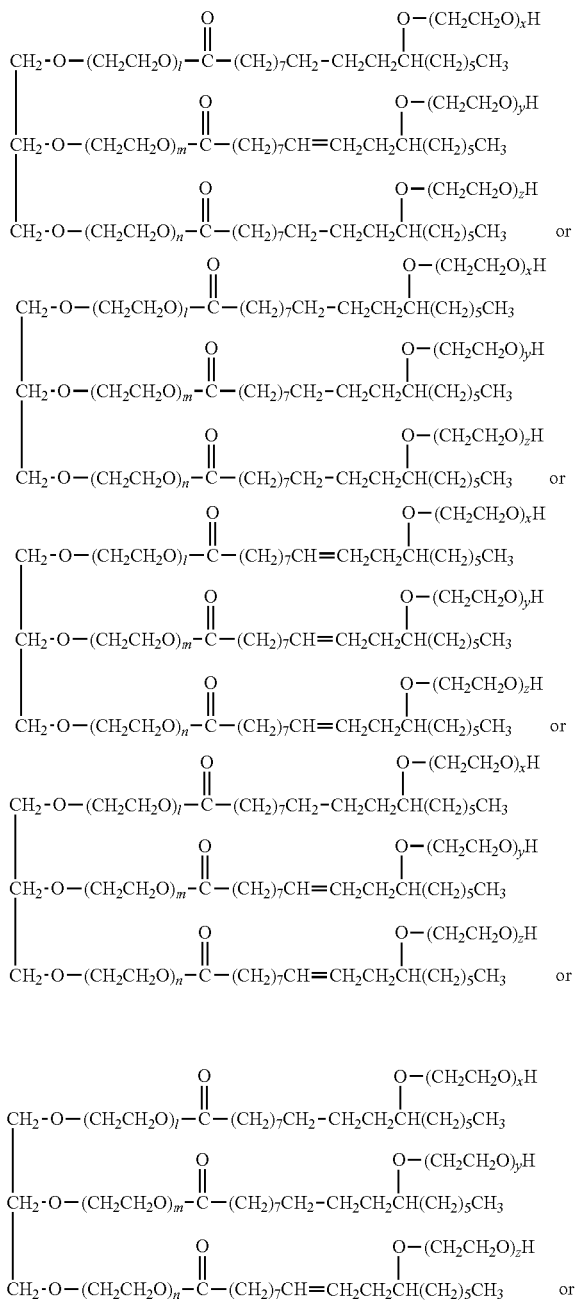

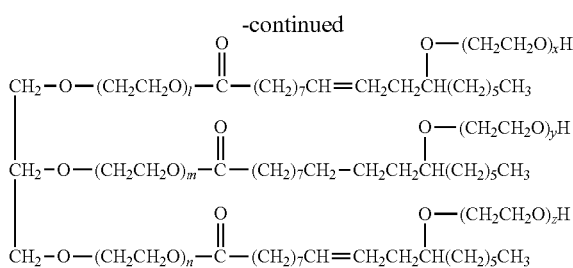

These ethoxylates can be used alone or in any mixture thereof. The average ethylene oxide addition mole number (i.e., $1+m+n+x+y+z$ in the above formula) of these ethoxylates is generally from about 7 to about 100, from about 20 to about 80, or different combinations of the upper and lower integers described above or combination of any integer n the ranges listed above.

Exemplary nonionic surfactants may include castor oil surfactants commercially available from Nikko under tradenames HCO 40 and HC060, from BASF under the tradenames Cremophor RH40, RH60 and CO60, Basophor ELH60, from The Dow Chemical Company under the tradenames Tergitol™ ECO-20, Tergitol™ ECO-36 and TergitolTMECO-40.

Further examples of nonionic surfactants may include condensates of from 3 to 30 moles of ethylene oxide with an aliphatic alcohol of 8 to 22 carbon atoms, condensates of 5 to 30 moles of ethylene oxide with an alkyl phenol wherein the alkyl contains 9 to 15 carbon atoms and $C_8$ to $C_{22}$ alkyl dimethyl amine oxides. An exemplary nonionic surfactant may be a secondary alcohol ethoxylate known as Tergitol™ 15-S, available from The Dow Chemical Company.

Examples of ampholytic and zwitterionic surfactants are found in U.S. Pat. No. 3,929,678, Laughlin et al., issued Dec. 30, 1975 at Col, 19, line 38 through Col. 22 line 48. Examples of cationic surfactants are tetraalkyl quaternary ammonium salts having at least one alkyl chain of 8 to 22 carbon atoms, wherein the other alkyl groups can contain from 1 to 22 carbon atoms and wherein the anionic counterion is halogen ethylsulfate or methylsulfate.

G. Malodor Binding Polymer

The freshening composition of the present invention may comprise a malodor binding polymer. A malodor binding polymer is polymer having an available functional group (e.g. amine) that has the affinity to neutralize malodor components. Monomers having an available function group with an affinity to neutralize malodor components are also contemplated. In the case of amine based compounds, the amine will have an affinity for aldehyde malodors. The amine may react with aldehyde malodors and form a new compound, such as an aminol, imine, or enamine which is not odorous.

A malodor binding polymer may include amine based compounds, such as monoamines, amino acids, polyethyleneimine polymers (PEIs), modified PEIs, substituted PEIs; acrylic acid polymers, such as polyacrylate co-polymer (e.g. Acumer™ 9000 from Rohm & Haas), polyacrylic acid polymers (e.g. Acusol™ from Rohm & Haas), and modified acrylate copolymers (e.g. Aculyn™ from Rohm & Haas); and modified methacrylate copolymers (e.g. HydroSal™ from Salvona Technologies); or mixtures thereof.

1. Amine Based Compounds

The malodor binding polymer may be an amine based compound with a molecular weight greater than 100 Daltons and at least 10% of its amine groups are primary amines. The amine-based compound may be a polyamine with a molecular weight greater than 150 Daltons and 15% to 80% of its amine groups are primary amines. The malodor binding polymer may be an amine-based compound with a molecular weight greater than 1000 Daltons and from 0% to about 10% or less than 10% of its amine groups are primary amines.

A general structure for a primary amine compound useful in this invention is as follows:

wherein B is a carrier material, and n is an index of value of at least 1. Suitable B carriers include both inorganic and organic carrier moieties. By "inorganic carrier", it is meant a carrier which is comprised of non- or substantially non-carbon based backbones.

Compounds containing a secondary amine group have a structure similar to the above with the exception that the compound comprises one or more —NH— groups as well as —NH$_2$ groups. The amine compounds of this general type may be relatively viscous materials.

Exemplary amine based compounds are those selected from monoamines, aminoaryl derivatives, polyamines and derivatives thereof, polyamino acids and copolymers thereof, glucamines, dendrimers, PEIs, substituted amines and amides monoamines, or mixtures thereof.

a. Monoamines

Monoamines may be utilized in the present invention. Nonlimiting examples of suitable monoamines for use in the present invention include, but are not limited to, primary amines that also contain hydroxy and/or alkoxy functional groups, such as the 2-hydroxyamines and/or 3-hydroxyamines; primary or secondary amines that also contain a functional group that enhances deposition of the monoamine compared to monoamines that lack that functional group, especially when the monoamine is interacting with the benefit agent. Primary monoamines may also be used herein in combination with secondary monoamines. However, sufficient levels of the primary monoamine must be used to provide at least 10% of the total amine groups within such combinations as primary amine groups.

b. Aminoaryl Derivatives

Exemplary aminoaryl derivatives are the amino-benzene derivatives including the alkyl esters of 4-amino benzoate compounds, ethyl-4-amino benzoate, phenylethyl-4-aminobenzoate, phenyl-4-aminobenzoate, 4-amino-N'-(3-aminopropyl)-benzamide, or mixtures thereof.

c. Polyamines

Examples of suitable amino functional polymers containing at least one primary amine group for the purposes of the present invention are: Polyvinylamine with a MW of 300-2.10E6 Daltons (e.g Lupamine series 1500, 4500, 5000, 9000 available from BASF); Polyvinylamine alkoxylated with a MW of ≥600 Daltons and a degree of ethoxylation of at least 0.5; Polyvinylamine vinylalcohol-molar ratio 2:1, polyvinylaminevinylformamide-molar ratio 1:2 and polyvinylamine vinylformamide-molar ratio 2:1; Triethylenetetramine, diethylenetriamine, tetraethylenepentamine; Bis-aminopropylpiperazine; amino substituted polyvinylalcohol with a MW ranging from 400-300,000 Daltons; polyoxyethylene bis[amine] available from e.g. Sigma; polyoxyethylene bis[6-aminohexyl] available from e.g. Sigma; N,N'-bis-(3-aminopropyl)-1,3-propanediamine linear or branched (TPTA); N,N'-bis-(3-aminopropyl)ethylenediamine; bis (amino alkyl)alkyl diamine, linear or branched; and 1,4-bis-(3-aminopropyl)piperazine (BNPP).

d. Polyamino Acids

Suitable amine based compounds include polyamino acids. Polyamino acids are made up of amino acids or chemically modified amino acids. The amino acids may be selected from cysteine, histidine, isoleucine, tyrosine, tryptophane, leucine, lysine, glutamic acid, glutamine, glycine, alanine, aspartic acid, arginine, asparagine, phenylalanine, proline, serine, histidine, threonine, methionine, valine, and mixtures thereof. Amino acid derivatives may be tyrosine ethylate, glycine methylate, tryptophane ethylate, or mixtures thereof homopolymers of amino acids; hydroxyamines; polyamino acids; or mixtures thereof.

In chemically modified amino acids, the amine or acidic function of the amino acid has reacted with a chemical reagent. This is often done to protect these chemical amine and acid functions of the amino acid in a subsequent reaction or to give special properties to the amino acids, like improved solubility. Examples of such chemical modifications are benzyloxycarbonyl, aminobutyric acid, butyl ester, and pyroglutamic acid. More examples of common modifications of amino acids and small amino acid fragments can be found in the Bachem, 1996, Peptides and Biochemicals Catalog.

One polyamino acid is polylysine, alternatively polylysines or polyamino acids where more than 50% of the amino acids are lysine, since the primary amine function in the side chain of the lysine is the most reactive amine of all amino acids. One polyamino acid has a molecular weight of 500 to 10,000,000, alternatively between 2000 and 25,000.

The polyamino acid can be cross linked. The cross linking can be obtained for example by condensation of the amine group in the side chain of the amino acid like lysine with the carboxyl function on the amino acid or with protein cross linkers like PEG derivatives. The cross linked polyamino acids still need to have free primary and/or secondary amino groups left for neutralization. Cross linked polyamino acid has a molecular weight of 20,000 to 10,000,000; alternatively between 200,000 and 2,000,000.

The polyamino acid or the amino acid can be co-polymerized with other reagents like for instance with acids, amides, acyl chlorides, aminocaproic acid, adipic acid, ethylhexanoic acid, caprolactam, or mixtures thereof. The molar ratio used in these copolymers ranges from 1:1 (reagent/amino acid (lysine)) to 1:20, alternatively from 1:1 to 1:10. The polyamino acid like polylysine can be unethoxylated or partially ethoxylated so long as the requisite amount of primary amine remains in the polymer.

e. Dendrimers

Also useful amine based compounds are polypropylenimine dendrimers and the commercially available Starburst® polyamidoamines (PAMAM) dendrimers, generation GO-G10 from Dendritech and the dendrimers Astromols®, generation 1-5 from DSM being DiAminoButane PolyAmine DAB (PA)x dendrimers with x=2<n>x4 and n being generally comprised between 0 and 4.

f PEIs

In one embodiment, the malodor binding polymer is a PEI. It has been surprisingly discovered that amine based polymers at a pH of about 4 to about 8, alternatively above 5 to about 8, alternatively 7 can neutralize amine based odors. PEIs have the following general formula:

Homopolymeric PEIs are branched, spherical polyamines with a well defined ratio of primary, secondary and tertiary amine functions. They are best described in the following partial structural formula:

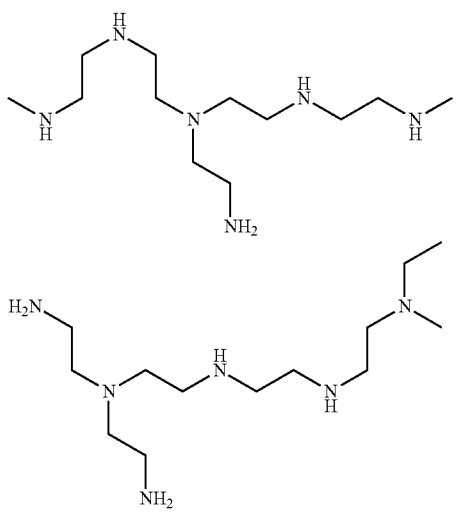

The chemical structure of homopolymeric PEIs follows a simple principle: one amine function—two carbons.

The freshening composition may comprise a homopolymeric polyethylenimine having a molecular weight of about 800 to about 2,000,000, alternatively about 1,000 to about 2,000,000, alternatively about 1,200 to about 25,000, alternatively about 1,300 to about 25,000, alternatively about 2,000 to about 25,000, alternatively about 10,000 to about 2,000,000, alternatively about 25,000 to about 2,000,000, alternatively about 25,000. Exemplary homopolymeric PEIs include those that are commercially available under the tradename Lupasol® from BASF. Lupasol products are usually obtained through polymerization of the ethylenimine monomer. The ethylenimine monomer has totally reacted in the polymer matrix. Suitable Lupasol products include Lupasol FG (MW 800), G20wfv (MW 1300), PR8515 (MW 2000), WF (MW 25,000), FC (MW 800), G20 (MW 1300), G35 (MW 1200), G100 (MW 2000), HF (MW 25,000), P (MW 750,000), PS (MW 750,000), SK (MW 2,000,000), SNA (MW 1,000,000).

The freshening composition may comprise Lupasol HF or WF (MW 25,000), P (MW 750,000), PS (MW 750,000), SK (MW 2,000,000), G20wfv (MW 1300) or PR 1815 (MW 2000), or Epomin SP-103, Epomin SP-110, Epomin SP-003, Epomin SP-006, Epomin SP-012, Epomin SP-018, Epomin SP-200, or partially alkoxylated polyethyleneimine, like polyethyleneimine 80% ethoxylated from Aldrich. The freshening composition may comprise Lupasol WF (MW 25,000).

Also suitable amine based compounds for use in the freshening composition are modified PEIs, partially alkylated polyethylene polymers, PEIs with hydroxyl groups, 1,5-pentanediamine, 1,6-hexanediamine, 1,3 pentanediamine, 3-dimethylpropanediamine, 1,2-cyclohexanediamine, 1,3-bis(aminomethyl)cyclohexane, tripropylenetetraamine, bis(3-aminopropyl)piperazine, dipropylenetriamine, tris(2-aminoethylamine), tetraethylenepentamine, bishexamethylenetriamine, bis(3-aminopropyl) 1,6-hexamethylenediamine, 3,3'-diamino-N-methyl-dipropylamine, 2-methyl-1,5-pentanediamine, N,N,N',N'-tetra(2-aminoethyl)ethylenediamine, N,N,N',N'-tetra(3-aminopropyl)-1,4-butanediamine, pentaethylhexamine, 1,3-diamino-2-propyl-tert-butylether, isophorondiamine, 4,4',-diaminodicyclohylmethane, N-methyl-N-(3-aminopropyl)ethanolamine, spermine, spermidine, 1-piperazineethaneamine, 2-(bis(2-aminoethyl)amino)ethanol, ethoxylated N-(tallowalkyl)trimethylene diamines, poly[oxy(methyl-1,2-ethanediyl)], α-(2-aminomethylethoxy)- (=C.A.S No. 9046-10-0); poly[oxy(methyl-1,2-ethanediyl)], α-hydro-ω-(2-aminomethylethoxy)-, ether with 2-ethyl-2-(hydroxymethyl)-1,3-propanediol (=C.A.S, No. 39423-51-3); commercially available under the tradename Jeffamines T-403, D-230, D-400, D-2000; 2,2',2"-triaminotriethylamine; 2,2'-diamino-diethylamine; 3,3'-diamino-dipropylamine, 1,3 bis aminoethyl-cyclohexane commercially available from Mitsubishi, and the C12 Sternamines commercially available from Clariant like the C12 Sternamin(propylenamine)n with n=3/4.

Suitable levels of malodor binding polymer are from about 0.01% to about 2%, alternatively from about 0.01% to about 1%, alternatively about 0.01% to about 0.8%, alternatively about 0.01% to about 0.6%, alternatively about 0.01% to about 0.1%, alternatively about 0.01% to about 0.07%, alternatively about 0.07%, by weight of the freshening composition. Compositions with higher amount of malodor binding polymer may make fabrics susceptible to soiling and/or leave unacceptable visible stains on fabrics as the solution evaporates off of the fabric.

H. Malodor Counteractant

The freshening composition may utilize one or more malodor counteractants. Malodor counteractants may include components which lower the vapor pressure of odorous compounds, solubilize malodor compounds, physically entrap odors (e.g. flocculate or encapsulate), physically bind odors, or physically repel odors from binding to inanimate surfaces. For example, aliphatic aldehydes react with amine odors, such as fish and cigarette odors. When used in combination with the malodor binding polymer, the freshening composition may neutralize a broader range of malodor causing materials which, in turn, further reduces malodors in the air or on inanimate surfaces.

Specifically, the freshening composition may include a malodor counteractant, wherein the malodor counteractant is selected from the group consisting of: polyols, cyclodextrin and derivatives thereof, amine functional polymers, aldehydes, and combinations thereof. The malodor counteract may be cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

I. Buffering System

The freshening composition may include a buffering agent. The buffering agent may be an acidic buffering agent. The buffering agent may be a dibasic acid, carboxylic acid, dicarboxylic acid such as maleic acid, tricarboxylic acid such as citric acid, or a polycarboxylic acid such as polyacrylic acid. The carboxylic acid may be, for example, citric acid, polyacrylic acid, or maleic acid. The acid may be sterically stable. The acid may be used in the composition for maintaining the desired pH. The freshening composition may have a pH from about 4 to about 9, alternatively from about 4 to about 8.5, alternatively from about 4 to about 6.9, alternatively about 4 to about 6.7. Preferably, the buffer system comprises one or more buffering agents selected from the group consisting of: citric acid, maleic acid, polyacrylic acid, and combinations thereof. It has been found that buffer systems that include a buffering agent selected from the group consisting of: citric acid, maleic acid, polyacrylic acid, and combinations thereof provide stable freshening compositions with prolonged shelf life.

Preferably, the buffer system comprises citric acid and sodium citrate. It has been found that buffer systems comprising citric acid and sodium citrate provide stable freshening compositions with a prolonged shelf life. Other suitable buffering agents for the freshening compositions include biological buffering agents. Some examples are nitrogen-containing materials, sulfonic acid buffers like 3-(N15489 morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine or methyldiethanolamine or derivatives thereof. Other nitrogen containing buffering agents are tri(hydroxymethyl)amino methane (HOCH2)5 3CNH3 (TRIS), 2-amino-2-ethyl-1,3-propanediol, 2-amino-2-methylpropanol, 2-amino-2-methyl-1,3-propanol, disodium glutamate, N-methyl diethanolamide, 2-dimethylamino-2-methylpropanol (DMAMP), 1,3-bis (methylamine)-cyclohexane, 1,3-diamino-propanol N,N'-tetra-methyl-1,3-diamino-2-propanol, N,N-bis(2-hydroxyethyl)glycine (bicine) and N-tris (hydroxymethyl) methyl glycine (tricine). Mixtures of any of the above are also acceptable.

The freshening compositions may include a secondary or tertiary amine. The freshening compositions may contain at least about 0%, alternatively at least about 0.001%, alternatively at least about 0.01%, by weight of the composition, of a buffering agent. The composition may also contain no more than about 2%, alternatively no more than about 0.75%, alternatively no more than about 0.5%, by weight of the composition, of a buffering agent.

J. Wetting Agent

The freshening composition may, optionally, include a wetting agent that provides a low surface tension that permits the composition to spread readily and more uniformly on hydrophobic surfaces like polyester and nylon. It has been found that the freshening composition, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives and perfumes in the concentrated freshening compositions. Non-limiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as C12-18 aliphatic alcohols, are not generally compatible with the cyclodextrin. Certain of the block polymer surfactant compounds designated Pluronic™ and Tetronic™ by the BASF-Wyandotte Corp., Wyandotte, Mich., are readily available.

Non-limiting examples of cyclodextrin-compatible wetting agents of this type are described in U.S. Pat. No. 5,714,137 and include the SILWET™ surfactants available from Momentive Performance Chemical, Albany, N.Y. Exemplary SILWET™ surfactants are as follows in Table 6 below. However, it will be appreciated that mixtures of the following surfactants may also be used in the present invention.

TABLE 6

| SILWET ™ Surfactants | Average MW |
|---|---|
| L-7608 | 600 |
| L-7607 | 1,000 |
| L-77 | 600 |
| L-7605 | 6,000 |
| L-7604 | 4,000 |
| L-7600 | 4,000 |
| L-7657 | 5,000 |

The total amount of surfactants (e.g. solubilizer, wetting agent) in the freshening composition is from 0 wt. % to about 3 wt. % or no more than 3 wt. %, alternatively from 0 wt. 5% to about 1 wt. % or no more than 1 wt. %, alternatively from 0 wt. % to about 0.9 wt. % or no more than 0.9 wt. %, alternatively from 0 wt. % to about 0.7 wt. % or no more than 0.7 wt. %, alternatively from 0 wt. % to about 0.5 wt. % or no more than 0.5 wt. %, alternatively from 0 wt. % to 0.3 wt. % or no more than about 0.3 wt. %, by weight of the composition. Compositions with higher concentrations can make fabrics susceptible to soiling and/or leave unacceptable visible stains on fabrics as the solution evaporates. The weight ratio of sulfur containing pro-perfume to total surfactant may be from about 1:1 to 1:250, or from about 1:1 to about 1:60, or from about 1:1 to about 1:30.

II. Method of Manufacture

The freshening composition can be made in any suitable manner known in the art. All of the ingredients can simply be mixed together. In certain embodiments, it may be desirable to make a concentrated mixture of ingredients such as a pre-mix and dilute by adding the same to an aqueous carrier before dispersing the composition into the air or on an inanimate surface. A method of manufacturing a freshening composition may comprise the steps of:

i) mixing alkoxylated phenol and perfume to form a pre-mix, wherein the weight ratio of the alkoxylated phenol to the perfume is 0.01:1 to 100:1, preferably 0.1:1 to 10:1, even more preferably 0.15:1 to 1:1; and ii) adding the premix to the water to form the freshening composition.

In another embodiment, the ethoxylated phenol may be dispersed in one vessel containing ingredients such as water and may contain additional ingredients such as ethanol, low molecular polyols, and buffer agents. All materials are added until fully dispersed and visually dissolved. In a separate vessel, the solubilizing materials (surfactants and solvents, and in some embodiments may contain the ethoxylated phenol) and perfume are mixed until homogenous. The solution of solubilizing materials and perfume are then added to the first mixing vessel, and mixed until homogenous.

III. Method of Use

The freshening composition can be used by dispersing, e.g., by placing the freshening composition into a dispenser, such as a spray dispenser and spraying an effective amount into the air or onto the desired inanimate surface or article. "Effective amount", when used in connection with the amount of the freshening composition, means an amount sufficient to provide at least about 4 hours, or at least about 6 hours, or at least about 8 hours, or at least about 24 hours of freshness or scent to the treated air, surface, or article, yet not so much as to saturate or create a pool of liquid on an article or surface and so that, when dry, there is no visual deposit readily discernible. Where malodor reducing ingredients are included, "effective amount", when used in connection with the amount of the freshening composition, means an amount that provides the foregoing and also provides neutralization of a malodor to the point that it is not discernible by the human sense of smell, yet not so much as to saturate or create a pool of liquid on an article or surface and so that, when dry, there is no visual deposit readily discernible. Dispersing can be achieved by using a spray device, a roller, a pad, or other product forms described hereinafter.

Product Forms

Wipes

The freshening compositions of the present invention may be impregnated into a commercially available substrate such as the substrates discussed in U.S. RE38505, U.S. RE38105, and U.S. Pat. No. 6,936,330, all of which are incorporated herein by reference. In one embodiment, the substrate may be a non-woven, wet-wipe for deodorizing, disinfecting, or cleaning multiple surfaces including inanimate household surfaces.

Packaging Container

The freshening compositions of the present invention can be contained in plastic containers constructed of hydrophilic perfume compatible materials. These materials avoid complexing, with hydroplilic perfume ingredients, such that absorption by and/or transmission through plastic containers is minimized. Suitable hydrophilic perfume compatible materials can be readily identified by determining the average hydrophilic perfume loss through gas chromatography analysis. Hydrophilic perfume compatible materials result in an average hydrophilic perfume ingredient loss of less than about 50% alternatively less than about 20%, alternatively less than about 15% and alternatively less than about 10% of the originally present individual hydrophilic perfume ingredients.

Freshening compositions containing a substantial amount of hydrophilic perfume ingredients can be stored in plastic container constructed of at least 80% hydrophilic perfume compatible materials for 8 weeks at ambient temperature. After storage, gas chromatography analysis is used to determine the amount of the various perfume ingredients remaining in the aqueous composition and approximate loss is calculated based on the amount of each ingredient originally present.

An effective amount of hydrophilic perfume compatible materials suitable for the present invention is at least about 80%, alternatively about 80% to about 100%, alternatively about 90% to about 100%, and alternatively 100%, by weight of the container. Non-limiting examples of hydrophilic perfume compatible materials are any resins of high density polyethylene (HDPE), low density polyethylene (LDPE), polyvinyl chloride (PVC), polypropylene (PP), polystyrene (PS), polyethylene-co-vinyl alcohol (EVOH), fluorinated polymer such as Aclar®, acrylonitrile-methyl acrylate copolymer such as Barex®, or mixtures thereof. Alternatively HDPE is utilized in the present invention.

In one embodiment, an HDPE bottle, from Plastipak Packaging Inc. Champaign, Ill., is used to contain the aqueous composition of the present invention. HDPE bottles can be made by any blow molding, injection molding, and thermoform process known in the art. For example, for blow molded bottles, heat softened HDPE is extruded as a hollow tube into a mold cavity and forced by pressurized air against the walls of the cold mold cavity to form the bottle. The bottle solidifies by cooling.

It has been found that the perfume compositions having a Clog P of less than about 3 are not fully absorbed into and/or transmitted through the hydrophilic perfume compatible materials such as PP and HDPE. Thus, this assists in preventing transmission of perfume ingredients through plastic containers; which in turn provides consumer noticeable longer lasting fragrance life.

Any of the hydrophilic perfume compatible materials can be used in conjunction with one or more barrier materials including amorphous carbon, silicone oxide or mixtures thereof and metallized coating.

Freshening Product

The freshening composition can be packaged in any suitable package to form a freshening product. The package may be in the form of a spray dispenser and the freshening product may be a freshening sprayer product. The spray dispenser may be transparent or translucent such that the freshening composition is visible or at least partially visible from outside of the freshening product.

The spray dispenser may hold various amounts of freshening composition. The spray dispenser may be capable of withstanding internal pressure in the range of about 20 p.s.i.g. to about 140 psig, alternatively about 80 to about 130 p.s.i.g. The total composition output and the spray droplet/particle size distribution may be selected to support the particulate removal efficacy but avoid a surface wetness problem. Total output is determined by the flow rate of the composition as it is released from the spray dispenser. To achieve a spray profile that produces minimal surface wetness, it is desirable to have a low flow rate and small 5 spray droplets.

The flow rate of the composition being released from the spray dispenser may be from about 0.0001 grams/second (g/s) to about 2.5 grams/second. Alternatively, the flow rate may be from about 0.001 grams/second to about 2.5 grams/second, or about 0.01 grams/second to about 2.0 grams/second. For an aerosol sprayer, the flow rate is determined by measuring the rate of composition expelled by a spray dispenser for any 60 second period of use.

The Sauter Mean Diameter of the spray droplets may be in the range of from about 10 µm to about 100 µm, alternatively from about 20 µm to about 60 µm. At least some of the spray droplets are sufficiently small in size to be suspended in the air for at least about 10 minutes, and in some cases, for at least about 15 minutes, or at least about 30 minutes. Small particles can be efficiently created when the spray is dispensed in a wide cone angle. For a given nozzle component and delivery tube, cone angles can be modified by varying the insertion depth of the nozzle in the delivery tube. The cone angle may be greater than about 20 degrees, or greater than about 30 degrees, or greater than about 35 degrees, or greater than about 40 degrees, or greater than about 50 degrees.

The spray dispenser may be configured to spray the freshening composition at an angle that is between an angle that is parallel to the base of the container and an angle that is perpendicular thereto. The desired size of spray droplets can be delivered by other types of spray dispensers that are capable of being set to provide a narrow range of droplet size. Such other spray dispensers include, but are not limited to: foggers, ultrasonic nebulizers, electrostatic sprayers, and spinning disk sprayers. The spray dispenser may be comprised of various materials, including plastic, metal, glass, or combinations thereof. The spray dispenser may be pressurized, unpressurized or non-aerosol.

A non-aerosol spray dispenser may include a pre-compression trigger sprayer.

One suitable non-aerosol spray dispenser is a plastic non-aerosol dispenser. The dispenser may be constructed of polyethylene such as a high-density polyethylene; polypropylene; polyethyleneterephthalate ("PET"); vinyl acetate, rubber elastomer, and combinations thereof. The spray dispenser may be made of clear PET. Another suitable spray dispenser includes a continuous action sprayer, such as FLAIROSOL™ dispenser from Afa Dispensing Group. The FLAIROSOL™ dispenser includes a bag-in-bag or bag-in-can container with a pre-compression spray engine, and aerosol-like pressurization of the freshening composition. An example of the FLAIROSOL™ dispenser is described in U.S. Pat. No. 8,905,271B2.

A pressurized spray dispenser may include a propellant. Various propellants may be used. The propellant may comprise hydrocarbon(s); compressed gas(es), such as nitrogen, carbon dioxide, air; liquefied gas(es) or hydrofluoro olefin ("HFO"); and mixtures thereof. Preferably, the product comprises a propellant selected from the group consisting of compressed gas such as compressed air, compressed nitrogen, and combinations thereof. Propellants listed in the U.S. Federal Register 30 49 C.F.R. § 1.73.115, Class 2, Division 2.2 are considered acceptable. The propellant may particularly comprise a trans-1,3,3,3-tetrafluoroprop-1-ene, and optionally a CAS number 1645-83-6 gas. Such propellants provide the benefit that they are not flammable, although the freshening compositions are not limited to inflammable propellants. One such propellant is commercially available from Honeywell International of Morristown, N.J. under the trade name HFO-5 1234ze or GWP-6. If desired, the propellant may be condensable. By "condensable", it is meant that the propellant transforms from a gaseous state of matter to a liquid state of matter in the spray dispenser and under the pressures encountered in use. Generally, the highest pressure occurs after the spray dispenser is charged with a freshening composition but before that first dispensing of that freshening composition by the user. A condensable propellant provides the benefit of a flatter depressurization curve as the freshening composition is depleted during usage.

The pressurized spray dispenser may be free of a hydrocarbon propellant. The freshening composition may be delivered from the spray dispenser which includes delivery components including but not limited to a valve to control flow and to seal the freshening composition within the spray dispenser, a button actuator and a nozzle for dispensing the freshening composition to the environment. The freshening composition may be contained in a bag-in-can plastic spray dispenser.

The following examples are intended to more fully illustrate the present invention and are not to be construed as limitations of the present invention since many variations thereof are possible without departing from the scope of the present invention. All parts, percentages and ratios used herein are expressed as percent weight unless otherwise specified.

EXAMPLES

Test equipment/materials and test fabric freshening compositions are first described under Materials, then Test Methods are provided, and lastly results are discussed. Data is provided demonstrating the fabric freshening compositions of the present invention having improved solubility of PRMs in the fabric freshening compositions. Equipment and materials for making the freshening compositions used in the Test Methods described hereinafter are listed in Table 7 and Table 8 below. The formulations of inventive and comparative fabric freshening compositions are provided in Examples I, II, III below.

TABLE 7

| Equipment/Materials | | | |
|---|---|---|---|
| Component (Ingredient) | Example | CAS | Commercial Name |
| Aqueous Carrier | Water | 7732-18-5 | Water |
| Solvent for PRM | Ethanol | 64-17-5 | Ethanol |
| Ethoxylated Phenol for PRM | HEXAETHYLENE GLYCOL PHENYL ETHER | 9004-78-8 | Dowanol ™ EPh6 Glycol Ether |
| Ethoxylated Phenol for PRM | Ethylene Glycol Phenyl Ether | 122-99-6 | Dowanol ™ EPh Glycol Ether |
| Ethoxylated Phenol for PRM | Diethylene Glycol Phenyl Ether | 104-68-7 | Dowanol ™ DiEPh Glycol Ether |
| Malodor Counteractant Polymer | Polyethyleneimine | 9002-98-6 | Lupasol HF |
| Solvent for Malodor Counteractant Polymer | Diethylene Glycol | 111-46-6 | Diethylene Glycol |
| Wetting Agent/Spreading Polymer | Polyalkyleneoxide Modified Polydimethylsiloxane | 68938-54-5 | Silwet L7600 |
| Wetting Agent/Spreading Material Surfactant | Didecyl dimethylammoium chloride | 7173-51-5 | Uniquat 2250 |
| Buffering Agent | Maleic Acid | 110-16-7 | Maleic Acid |
| Preservative | Benzisothiazolinone | 2634-33-5 | Koralone B-119 |

TABLE 7-continued

| Equipment/Materials | | | |
|---|---|---|---|
| Component (Ingredient) | Example | CAS | Commercial Name |
| Buffering Agent | Citric Acid | 77-92-9 | Citric Acid |
| Buffering Agent | Sodium Citrate | 6132-04-3 | Sodium Citrate |
| Perfume | Perfume Samples 1, 2, 3 as detailed in Table 8 | Not provided by manufacturer | Not provided by manufacturer |
| Surfactant | Hydrogenated, Ethoxylated Castor Oil | 61788-85-0 | Basophor ELH 60 |
| Surfactant | Ethoxylated Castor Oil | 61791-12-6 | Tergitol ECOsurf 36 |
| Surfactant | Dioctyl Sodium Sulfosuccinate | 577-11-7 | Aerosol OT-70 PG |
| Malodor Counteractant | Hydroxypropyl Beta Cyclodextrin | 128446-35-5 | Cavasol |
| Buffer | Sodium Hydroxide | 1310-73-2 | Sodium Hydroxide |
| Equipment | Supplier Name/Model No. | | |
| Balance | Metter Toledo/EP4102, (0.01 resolution) Mettler Toledo/PG503-S (0.001 resolution) | | |
| pH Meter | Thermo Scientific/EO8212 | | |
| Overhead mixing/magnetic stir bar equipment | IKA/RW20 VWR/58947-128 (A variety of stir bars are used dependent on the amount used for the samples- this is one example that can be used) | | |
| Turbidimeter | Hach/2100Q | | |

In the following experiments, the ethoxylated phenol used are commercially available hexaethylene glycol phenyl ether as described hereinbefore. However, it would be appreciated that hexaethylene glycol phenyl ether may be made according to the following method.

Method of Making Hexaethylene Glycol Phenyl Ether

Hexaethylene Glycol Phenyl Ether ("final product") is prepared according to the following steps:

1) Phenol (440 g, 4.68 mol) is melted at 55° C. under nitrogen, partially neutralized with solid KOH (2.6 g, 0.046 mol) and is added to a Parr Reactor which has been preheated to 65° C.
2) Water is removed in vacuo at 75° C., then the Parr Reactor is cooled to 70° C.
3) Ethylene oxide (7.04 mols) is added to the reactor portion-wise keeping the pressure below 75 psig and reacted at 70° C.
4) Once the addition step in (3) is complete, the reactor is heated to 90° C. and ethylene oxide (21.1 mols) is added portion-wise and is reacted at 90° C. keeping the pressure below 75 psig.
5) After the final addition when the pressure in the reactor leveled out, the reaction is stirred an additional 2 hours.
6) The reactor is cooled to 70° C. and residual ethylene oxide is removed in vacuo.
7) The final product is cooled to room temp and neutralized with acetic acid (2.7 g, 0.046 mol) to yield title product (99% yield).

It will be appreciated that one skilled can adapt the above method for making an Ethylene Glycol Phenyl Ether with any degree of alkoxylation ("final product"). The final product is determined by the moles of starting phenol and the moles of ethylene oxide added. So in the above example of preparing hexaethylene glycol phenyl ether, the method begins with 4.68 moles of phenol and adding a total of 28.1 moles of ethylene oxide in steps 3 and 4 to give a final product with average degree of alkoxylation of 6. If one was to want to make Pentadecaethylene Glycol Phenyl Ether having an average degree of alkoxylation of 15, the method may be modified to start step (1) with 4.68 moles of phenol, and a total of 70.2 moles of ethylene oxide may be added in steps 3 and 4.

For the test methods/calculations described hereinafter, any perfume suitable for use in sprayable air fresheners or vapor phase systems may be employed. For illustrative purposes as well as for the subsequent examples for fabric freshening compositions, the perfume may comprise of PRMs as shown in Table 8 below. The perfume, however, may constitute any number of materials suitable for freshening.

TABLE 8

| | Perfume Samples | | | |
|---|---|---|---|---|
| | Perfume Raw Material (PRM) | Perfume Sample 1 (approximately 60% of PRMs ClogP < 3), % by weight of the perfume composition | Perfume Sample 2 (approximately 80% of PRMs ClogP from 1-4.5), % | Perfume Sample 3 (approximately 80% of PRMs ClogP 3-10), % |
| 1 | Ethyl Maltol | 3 | 1.5 | 1 |
| 2 | Helional | 9 | 3 | 2 |
| 3 | HYDROXYCITRONELLAL | 8 | 3 | 2 |

TABLE 8-continued

Perfume Samples

| | Perfume Raw Material (PRM) | Perfume Sample 1 (approximately 60% of PRMs ClogP < 3), % by weight of the perfume composition | Perfume Sample 2 (approximately 80% of PRMs ClogP from 1-4.5), % | Perfume Sample 3 (approximately 80% of PRMs ClogP 3-10), % |
|---|---|---|---|---|
| 4 | Ethyl Vanillin | 3 | 1.5 | 1 |
| 5 | Pyranol | 8 | 3 | 2 |
| 6 | Benzyl acetate | 8 | 3 | 2 |
| 7 | Methyl Phenyl Carbinyl Acetate | 8 | 3 | 2 |
| 8 | Ligustral Or Triplal | 8 | 3 | 2 |
| 9 | Linalool | 8 | 3 | 2 |
| 10 | Cyclo Galbanate | 9 | 3 | 2 |
| 11 | UNDECALACTONE | 2 | 7 | 8 |
| 12 | Citronellol | 8 | 3 | 2 |
| 13 | LINALYL ACETATE | 2 | 7 | 8 |
| 14 | Verdox | 2 | 7 | 8 |
| 15 | 4-tertiary-Butyl cyclohexyl acetate | 2 | 7 | 8 |
| 16 | Orange Terpenes | 2 | 7 | 8 |
| 17 | Ethyl Trimethylcyclopenteene Butenol | 2 | 7 | 8 |
| 18 | Ionone Gamma Methyl | 2 | 7 | 8 |
| 19 | Hexyl salicylate | 2 | 7 | 8 |
| 20 | Habanolide 100% | 2 | 7 | 8 |
| 21 | Iso E super | 2 | 7 | 8 |
| | Total weight of PRMs having a ClogP < 3 | 64 | — | — |
| | Total weight of PRMs having a ClogP 1-4.5 | — | 77.5 | — |
| | Total weight of PRMs having ClogP 3-10 | | | 84 |
| | Total weight of the perfume composition | 100 | 100 | 100 |

Test Methods

A. Test Method for Measurement of NTU Turbidity

A turbidimeter is used to determine how well ingredients are able to solubilize and emulsify perfume. The method of measuring turbidity is described in detail in the following reference: Hach Company, 2009, 2013., "Hach 2100Q and 2100Qis User Manual."

This method of measurement determines quantitative values of turbidity by evaluating the ratio of a primary nephelometric light scatter signal to a transmitted light scatter signal. This particular method of evaluation provides values between 0 to 1000 Nephelometric Turbidity Units ("NTU"), where increasing NTU values indicate more turbid solutions. Thus, successful perfume emulsification will yield lower NTU values vs. unsuccessful perfume emulsification will yield higher NTU values. In between each test sample, water controls should be measured to ensure proper equipment operation.

B. Method for Calculation of Average Value of c of an Ethoxylated Phenol

This is a method for calculating the average value of c of an ethoxylated phenol according to Formula II:

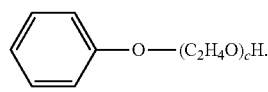
(II)

The individual weight % distributions for each ethoxylated species within an ethoxylated material are used to calculate the average value of c.

$$\text{average } c = \sum_{i=0}^{n} \frac{(x_i * i)}{100}$$

where i is an integer from 0 through n, representing the degree of ethoxylation $x_i$ is the weight % of individual species phenol ethoxylate i measured via GCFID method.

GCFID refers to known Gas Chromatography Flame Ionization Detection.

Example I

Fabric freshening compositions (Inventive Sample A and Comparative Samples B, C of Table 9) are evaluated according to qualitative visual appearance observation by the naked eye.

TABLE 9

| | Inventive Sample | Comparative Sample(s) | |
|---|---|---|---|
| Component | A | B | C |
| Water | Balance | Balance | Balance |
| Hexaethylene Glycol Phenyl Ether (average value of c = 6.18) | 3.00 | 0 | 0 |
| Diethylene Glycol Phenyl Ether (average value of c = 1.91) | 0 | 3.00 | 0 |
| Ethylene Glycol Phenyl Ether (average value of c = 1.00) | 0 | 0 | 3.00 |
| Polyethyleneimine | 0.07 | 0.07 | 0.07 |

TABLE 9-continued

| Component | Inventive Sample A | Comparative Sample(s) B | C |
|---|---|---|---|
| Diethylene Glycol | 0.18 | 0.18 | 0.18 |
| Polyalkyleneoxide Modified Polydimethylsiloxane | 0.10 | 0.10 | 0.10 |
| Didecyl dimethylammoium chloride | 0.06 | 0.06 | 0.06 |
| Maleic Acid | 0.06 | 0.06 | 0.06 |
| Benzisothiazolinone | 0.02 | 0.02 | 0.02 |
| Citric Acid | 0.02 | 0.02 | 0.02 |
| Perfume Sample 3 | 0.1 | 0.1 | 0.1 |
| Ethoxylated Castor Oil | 0.05 | 0.05 | 0.05 |
| Hydroxypropyl Beta Cyclodextrin | 0.63 | 0.63 | 0.63 |
| Sodium Hydroxide | Trim to target pH | Trim to target pH | Trim to target pH |
| Target pH | 6-7 | 6-7 | 6-7 |
| Visual Appearance Observations | Clear | Turbid | Turbid |

The results in Table 9 show that a visual appearance of Inventive Sample A is clear relative to Comparative Samples B, C which demonstrate turbid appearances.

Example II

Table 10 describes fabric freshening compositions which are evaluated according to the Test Method for Turbidity described hereinbefore under Test Methods. All test fabric freshening compositions in Table 10 are prepared as indicated in Method of Manufacturing to obtain eighteen (18) fabric freshening compositions, and turbidity results thereof are shown in Table 11 below.

TABLE 10

Fabric Freshening Composition Samples

| Ingredient (% by weight of the Freshening Composition) | Comparative Sample(s) | | Inventive Sample(s) | | | |
|---|---|---|---|---|---|---|
| | D | E | F | G | H | I |
| Water | Balance | Balance | Balance | Balance | Balance | Balance |
| Ethanol | 3.00 | 3.00 | 3.00 | 0 | 0 | 0 |
| Ethoxylated Phenol | 0 | 0 | 0 | 3.00 | 3.00 | 3.00 |
| Polyethyleneimine | 0.07 | 0.07 | 0.07 | 0.07 | 0.07 | 0.07 |
| Diethylene Glycol | 0.18 | 0.18 | 0.18 | 0.18 | 0.18 | 0.18 |
| Polyalkyleneoxide Modified Polydimethylsiloxane | 0.10 | 0.10 | 0.10 | 0.10 | 0.10 | 0.10 |
| Didecyl dimethylammonium chloride | 0.06 | 0.06 | 0.06 | 0.06 | 0.06 | 0.06 |
| Maleic Acid | 0.06 | 0.06 | 0.06 | 0.06 | 0.06 | 0.06 |
| Benzisothiazolinone | 0.02 | 0.02 | 0.02 | 0.02 | 0.02 | 0.02 |
| Citric Acid | 0.02 | 0.02 | 0.02 | 0.02 | 0.02 | 0.02 |
| Perfume Sample(s) 1, 2, 3 | 0.10 | 0.10 | 0.10 | 0.10 | 0.10 | 0.10 |
| Hydrogenated, Ethoxylated Castor Oil | 0.05 | 0 | 0 | 0.05 | 0 | 0 |
| Ethoxylated Castor Oil | 0 | 0.05 | 0.05 | 0 | 0.05 | 0.05 |
| Ethoxylated Phenol Premixed with Fragrance | 0 | 0 | 0.05 | 0 | 0 | 0.05 |
| Hydroxypropyl Beta Cyclodextrin | 0.63 | 0.63 | 0.63 | 0.63 | 0.63 | 0.63 |
| Sodium Hydroxide | Trim to target pH | Trim to target pH | Trim to target pH | Trim to target pH | Trim to target pH | Trim to target pH |
| Total | 100 | 100 | 100 | 100 | 100 | 100 |
| Target pH | 6-7 | 6-7 | 6-7 | 6-7 | 6-7 | 6-7 |

*Various perfume compositions varied in hydrophobicity as indicated in Table 4

TABLE 11

| | Turbidity Results | | | | | |
|---|---|---|---|---|---|---|
| | Comparative Samples | | Inventive Samples | | | |
| | D, NTU | E, NTU | F, NTU | G, NTU | H, NTU | I, NTU |
| Perfume Sample 1 | 45.4 | 53.0 | 31.8 | 0.86 | 1.80 | 1.45 |
| Perfume Sample 2 | 175 | 304 | 32.8 | 16.1 | 8.13 | 2.41 |
| Perfume Sample 3 | 263 | 492 | 62.2 | 90.8 | 22.9 | 3.16 |

The turbidity results in Table 11 show that all 12 variations of the Inventive Samples F, G, H, I with any one of the Perfume Samples 1, 2, 3 have better NTU turbidity values relative to the corresponding 6 variations of Comparative Samples D, E.

Example III

Air freshening compositions (Inventive Sample J and Comparative Sample K of Table 13) are prepared with conventional methods and evaluated according to qualitative visual appearance observation by the naked eye.

TABLE 13

| Component | Inventive Sample J, wt % | Comparative Sample K, wt % |
|---|---|---|
| Water | Balance | Balance |
| Polyethylene Glycol Phenyl Ether | 4.90 | 0 |
| Ethanol | 4.50 | 9.80 |
| Citric Acid | 0.18 | 0.18 |
| Sodium Citrate | 0.30 | 0.30 |
| Dioctyl Sodium Sulfosuccinate | 0.14 | 0.14 |
| Perfume Sample 4 (Ingredients not disclosed by Manufacturer, comprises at least 60% of PRMs having ClogP > 1) | 1.50 | 1.50 |
| Hydrogenated, Ethoxylated Castor Oil (Basophor ELH 60) | 3.00 | 3.00 |
| Hydroxypropyl Beta Cyclodextrin | 0.15 | 0.15 |
| Benzisothiazolinone | 0.01 | 0.01 |
| Target pH | 4.5 to 5.5 | 4.5 to 5.5 |
| Making Appearance Grade | Clear | Clear |
| Cycle of 24 Hr −18° C. Freeze and 24 Hr Thaw at Room Temperature Appearance Grade | Clear | Turbid |

The results of Table 13 show that the Inventive Sample J using ethoxylated phenol and ethanol with PRMs meet phase stability requirements in that the appearance grade after making and freeze thaw cycling resulted in a clear visual appearance.

Example IV

Table 14 describes fabric freshening compositions which are evaluated according to the Test Method for Turbidity described hereinbefore under Test Methods. All test fabric freshening compositions in Table 14 are prepared as indicated in Method of Manufacturing and turbidity results thereof are shown in Table 15 below.

TABLE 14

| | Comparative Sample L, wt % | Comparative Sample M, wt % | Inventive Sample N, wt % | Comparative Sample O, wt % | Comparative Sample P, wt % | Inventive Sample Q, wt % |
|---|---|---|---|---|---|---|
| Water | Balance | Balance | Balance | Balance | Balance | Balance |
| Ethoxylated Phenol | 3.00 | 2.88 | 2.97 | 3.00 | 2.88 | 2.97 |
| Polyethyleneimine | 0.07 | 0.07 | 0.07 | 0.07 | 0.07 | 0.07 |
| Diethylene Glycol | 0.18 | 0.18 | 0.18 | 0.18 | 0.18 | 0.18 |
| Polyalkyleneoxide Modified Polydimethylsiloxane | 0.10 | 0.10 | 0.10 | 0.10 | 0.10 | 0.10 |
| Didecyl dimethylammoium chloride | 0.06 | 0.06 | 0.06 | 0.06 | 0.06 | 0.06 |
| Maleic Acid | 0.06 | 0.06 | 0.06 | 0.06 | 0.06 | 0.06 |
| Benzisothiazolinone | 0.02 | 0.02 | 0.02 | 0.02 | 0.02 | 0.02 |
| Citric Acid | 0.02 | 0.02 | 0.02 | 0.02 | 0.02 | 0.02 |
| Perfume Sample 5 (Ingredients not disclosed by Manufacturer, comprises at least 60% of PRMs having ClogP > 1) | 0.12 | 0.12 | 0.12 | 0.12 | 0.12 | 0.12 |
| Hydrogenated, Ethoxylated Castor Oil | 0 | 0 | 0 | 0.05 | 0.05 | 0.05 |
| Ethoxylated Castor Oil | 0.05 | 0.05 | 0.05 | 0 | 0 | 0 |
| Ethoxylated Phenol Premixed with Fragrance ("Pre-mix") | 0 | 0.12 | 0.03 | 0 | 0.12 | 0.03 |
| Hydroxypropyl Beta Cyclodextrin | 0.63 | 0.63 | 0.63 | 0.63 | 0.63 | 0.63 |
| Sodium Hydroxide | Trim to target pH | Trim to target pH | Trim to target pH | Trim to target pH | Trim to target pH | Trim to target pH |
| Total | 100 | 100 | 100 | 100 | 100 | 100 |
| Target pH | 6-7 | 6-7 | 6-7 | 6-7 | 6-7 | 6-7 |

TABLE 15

Turbidity Results

| | Comparative Example | Inventive Example | Comparative Example | | Inventive Example | |
|---|---|---|---|---|---|---|
| | ExampleL | Example M | Example N | Example O | Example P | Example Q |
| Ratio of ethoxylated phenol in premix to perfume | 0 | 1:1 | 0.25:1 | 0 | 1:1 | 0.25:1 |
| NTU | 18 | 21 | 9 | 40 | 68 | 21 |

As shown in Table 15, Inventive Sample N shows that a premix in an amount of and having a ratio of ethoxylated phenol to perfume of 0.25:1 provides improved turbidity results (NTU value of 9) relative to Comparative Sample L with no premix (NTU value of 18). Further Inventive Sample also shows improved turbidity results relative to Comparative Sample M with a premix in an amount of 0.12% (NTU value of 21).

Example V

Table 16 describes fabric freshening compositions which are evaluated according to the Test Method for Turbidity described hereinbefore under Test Methods.

TABLE 16

| Ingredient (% by weight of the Freshening Composition) | Inventive Sample R | Inventive Sample S | Inventive Sample T | Inventive Sample U |
|---|---|---|---|---|
| Water | Balance | Balance | Balance | Balance |
| Ethanol | 0 | 0 | 0 | 0 |
| Hexaethylene Glycol Phenyl Ether Commercially available Dowanol EPH6 Average degree of alkoxylation = 6 | 3.00 | 0 | 3.00 | 0 |
| Pentadecaethylene Glycol Phenyl Ether Experimental EPH15 Average degree of alkoxylation = 15 | 0 | 3.00 | 0 | 3.00 |
| Polyethyleneimine | 0.07 | 0.07 | 0.07 | 0.07 |
| Diethylene Glycol | 0.18 | 0.18 | 0.18 | 0.18 |
| Polyalkyleneoxide Modified Polydimethylsiloxane | 0.10 | 0.10 | 0.10 | 0.10 |
| Didecyl dimethylammoium chloride | 0.06 | 0.06 | 0.06 | 0.06 |
| Maleic Acid | 0.06 | 0.06 | 0.06 | 0.06 |
| Benzisothiazolinone | 0.02 | 0.02 | 0.02 | 0.02 |
| Citric Acid | 0.02 | 0.02 | 0.02 | 0.02 |
| Perfume Sample 3 | 0.07 | 0.07 | 0.20 | 0.20 |
| Surfactant TERGITOL ™ ECO-36, Ethoxylated Castor Oil | 0.05 | 0.05 | 0.10 | 0.10 |
| Hydroxypropyl Beta Cyclodextrin | 0.63 | 0.63 | 0.63 | 0.63 |
| Sodium Hydroxide | Trim to target pH | Trim to target pH | Trim to target pH | Trim to target pH |
| Total | 100 | 100 | 100 | 100 |
| Target pH | 6-7 | 6-7 | 6-7 | 6-7 |
| NTU Turbidity Results | 8 | 13 | 17 | 44 |

The above results show that use of ethoxylated phenols having an average degree of ethoxylation from 6 to 15 for solubilizing Perfume Sample 3, i.e. a perfume in which approximately 80% of PRMs have a ClogP from 3 to 10 demonstrates improved turbidity results.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A freshening composition comprising:
   at least 85% by weight of the freshening composition of water;
   a perfume, wherein the perfume comprises perfume raw materials in an amount of at least 60% by weight of the perfume, the perfume raw materials having a ClogP greater than 1.0;
   from about 0.1% to about 2% by weight of the freshening composition of polyethyleneimine; and
   at least 0.0015% by weight of the freshening composition of an alkoxylated phenol; wherein the alkoxylated phenol is according to Formula (I):

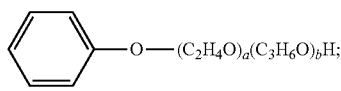 (I)

wherein a is a value selected from 3 to 15; b is a value selected from 0 to 12;
wherein the value of a +b, degree of alkoxylation is from 3 to 15.

2. The composition of claim 1, wherein the alkoxylated phenol is selected from the group consisting of: ethoxylated phenol, ethoxylated-propoxylated phenol, and combinations thereof.

3. The composition of claim 2, wherein the ethoxylated phenol is according to Formula (II):

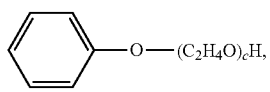 (II)

wherein an average value of c, degree of ethoxylation is $3 \leq c \leq 15$.

4. The composition of claim 1, wherein the alkoxylated phenol is in an amount of from 0.0015% to 9% by weight of the freshening composition.

5. The composition of claim 1, wherein the water is in an amount from 85% to 99.5% by weight of the freshening composition.

6. The composition according to claim 1, further comprising less than 3.5% of a surfactant by weight of the freshening composition, wherein the surfactant is selected from the group consisting of: nonionic surfactants, cationic surfactants, amphoteric surfactants, zwitterionic surfactants and mixtures thereof.

7. The composition according to claim 1, further comprising less than 10% of a solvent by weight of the freshening composition, wherein the solvent is selected from a group consisting of: an alcohol, a polyol and mixtures thereof.

8. The composition according to claim 7, wherein the solvent is ethanol, wherein the ethanol is in an amount of less than 10%, and wherein the ethanol and the alkoxylated phenol define a solvent system.

9. The composition according to claim 7, wherein the composition is substantially free of the solvent.

10. The composition of claim 1, wherein the perfume is in an amount of at least 0.001% by weight of the freshening composition.

11. The composition according to claim 1, wherein the perfume raw materials having ClogP greater than 1 are selected from the group consisting of: dihydro myrcenol, isonoyl alcohol, citronellol, tetrahydro linalool, tepinyl acetate, geranyl acetate, phenyl ethyl phenyl acetate, lilial P.T. Bucinal, 4-tert-butylcyclohexyl acetate, diphenyl methane, p-cymene, alpha pinene, benzyl salicylate, d-limonene, cis-hexenyl salicylate, hexyl cinnamic aldehyde, cedryl acetate, ethyl trimethylcyclopentene butanol, hexyl salicylate, ethyl vanillin, undecalactone, ionone gamma methyl, hydroxycitronellal, cyclo galbanate, 2-tert-butylcyclohexyl acetate, linalyl acetate, benzyl acetate, methyl phenyl carbinyl acetate, and mixtures thereof.

12. The composition according to claim 3, wherein an average value of c, the degree of ethoxylation is from 5 to 7, and wherein at least 80% by weight of the perfume of perfume raw materials have a ClogP greater than 2.0.

13. The composition according to claim 3, wherein the total weight ratio of the ethoxylated phenol to the perfume is 0.01:1 to 9,000:1.

14. The composition according to claim 1, wherein the freshening composition comprises a sulfur-containing pro-perfume.

15. The composition according to claim 14, wherein the sulfur-containing pro-perfume is a C4-C16 thio-damascone.

16. A non-aerosol freshening sprayer product comprising:
   a plastic container containing a freshening composition according to claim 1, wherein the plastic container comprises a material selected from the group consisting of: polypropylene, polyethylene terephthalate, high density polyethylene and combinations thereof.

17. A method of freshening comprising the step of spraying a freshening composition according to claim 1 onto a surface or into air.

* * * * *